(12) United States Patent
Stetter et al.

(10) Patent No.: US 8,884,382 B2
(45) Date of Patent: Nov. 11, 2014

(54) MULTI-DIMENSIONAL SENSORS AND SENSING SYSTEMS

(71) Applicant: KWJ Engineering Inc., Newark, CA (US)

(72) Inventors: Joseph R. Stetter, Hayward, CA (US); Amol G. Shirke, Newark, CA (US)

(73) Assignee: KWJ Engineering, Inc., Newark, CA (US)

( * ) Notice: Subject to any disclaimer, the term of this patent is extended or adjusted under 35 U.S.C. 154(b) by 0 days.

(21) Appl. No.: 13/868,583

(22) Filed: Apr. 23, 2013

(65) Prior Publication Data

US 2013/0311108 A1    Nov. 21, 2013

Related U.S. Application Data

(63) Continuation-in-part of application No. 13/271,659, filed on Oct. 12, 2011, now Pat. No. 8,426,932, which is a continuation-in-part of application No. 12/615,110, filed on Nov. 9, 2009, now Pat. No. 8,310,016, which is a continuation-in-part of application No. 11/879,462, filed on Jul. 17, 2007, now Pat. No. 7,911,010.

(51) Int. Cl.
| | |
|---|---|
| *H01L 27/14* | (2006.01) |
| *G01N 27/00* | (2006.01) |
| *A61B 5/0205* | (2006.01) |
| *A61B 5/021* | (2006.01) |
| *A61B 5/08* | (2006.01) |
| *A61B 5/1455* | (2006.01) |
| *A61B 5/024* | (2006.01) |

(52) U.S. Cl.
CPC ............... *G01N 27/00* (2013.01); *A61B 5/021* (2013.01); *A61B 5/0816* (2013.01); *A61B 5/14551* (2013.01); *A61B 5/0205* (2013.01); *A61B 2562/028* (2013.01); *A61B 5/024* (2013.01); *A61B 2560/0242* (2013.01)
USPC .......................................................... 257/414

(58) Field of Classification Search
CPC ................. A61B 5/0205; A61B 5/021; A61B 2562/028; A61B 5/0816; A61B 5/14551; A61B 2560/0242; A61B 5/024; G01N 27/00; G06F 19/3418
USPC ......... 257/414, 415; 204/406.408; 340/573.1, 340/573.12; 310/12.03; 600/365
See application file for complete search history.

(56) References Cited

U.S. PATENT DOCUMENTS

| | | | |
|---|---|---|---|
| 6,958,566 B2 * | 10/2005 | Nguyen et al. | 310/321 |
| 7,847,649 B2 * | 12/2010 | Van Beek et al. | 331/154 |

(Continued)

OTHER PUBLICATIONS

Aguilar, An Ultra-Low Power Microbridge Gas Sensor, ECS Transactions, 33(8), 245-253 (2010).

(Continued)

*Primary Examiner* — Nikolay Yushin
(74) *Attorney, Agent, or Firm* — Dinsmore & Shohl LLP

(57) ABSTRACT

A universal microelectromechanical (MEMS) nano-sensor platform having a substrate and conductive layer deposited in a pattern on the surface to make several devices at the same time, a patterned insulation layer, wherein the insulation layer is configured to expose one or more portions of the conductive layer, and one or more functionalization layers deposited on the exposed portions of the conductive layer to make multiple sensing capability on a single MEMS fabricated device. The functionalization layers are adapted to provide one or more transducer sensor classes selected from the group consisting of: radiant, electrochemical, electronic, mechanical, magnetic, and thermal sensors for chemical and physical variables and producing more than one type of sensor for one or more significant parameters that need to be monitored.

20 Claims, 38 Drawing Sheets

(56) References Cited

U.S. PATENT DOCUMENTS

| | | | |
|---|---|---|---|
| 8,471,714 B2* | 6/2013 | Reggiardo et al. | 340/573.1 |
| 2008/0148815 A1* | 6/2008 | Lucas et al. | 73/23.41 |
| 2010/0198023 A1* | 8/2010 | Yanai et al. | 600/301 |

OTHER PUBLICATIONS

Stetter, Introduction: Experimental Methods in Chemical Sensor and Sensor Array Evaluation and Development, Computational Methods for Sensor Material Selection, pp. 3-46, by Springer Science + Business Media, LLC, 2009.

* cited by examiner

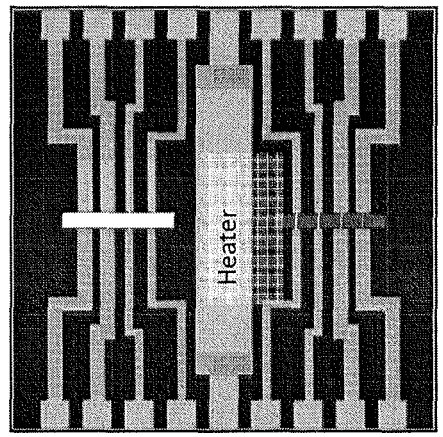
Figure 12: Polysilicon TCD bridge (Die 1,2, and 3.)

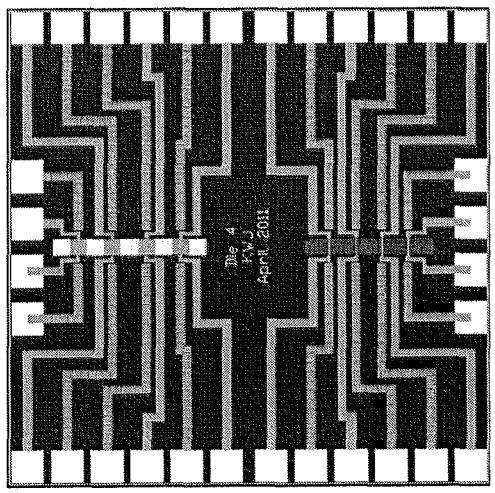
Figure 13: Polysilicon TCD bridge with Pt electrodes (Die 4 and 5.)

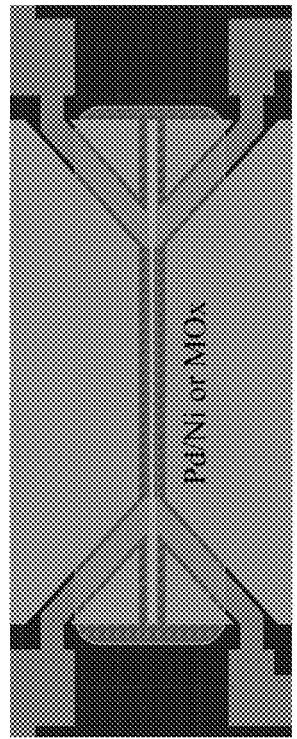
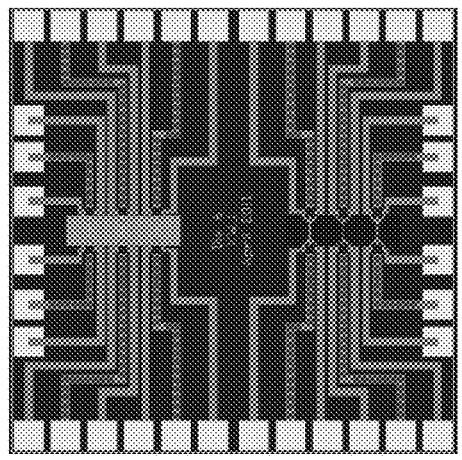
Figure 14: Polysilicon TCD bridge with Pt electrodes for 4-point R measurement (Die 6). The insert illustrates the area coated with a MOx or Pd film using shadow mask.

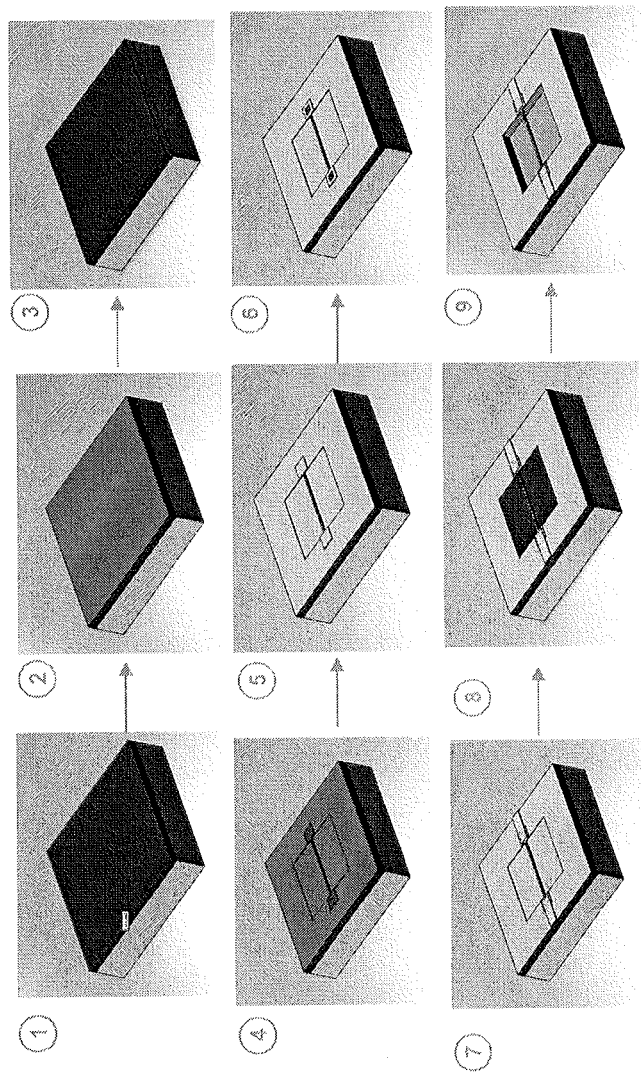
Figure 15: Illustration of processing of SiO2 coated Si wafer to fabricate Polysilicon TCD bridge.

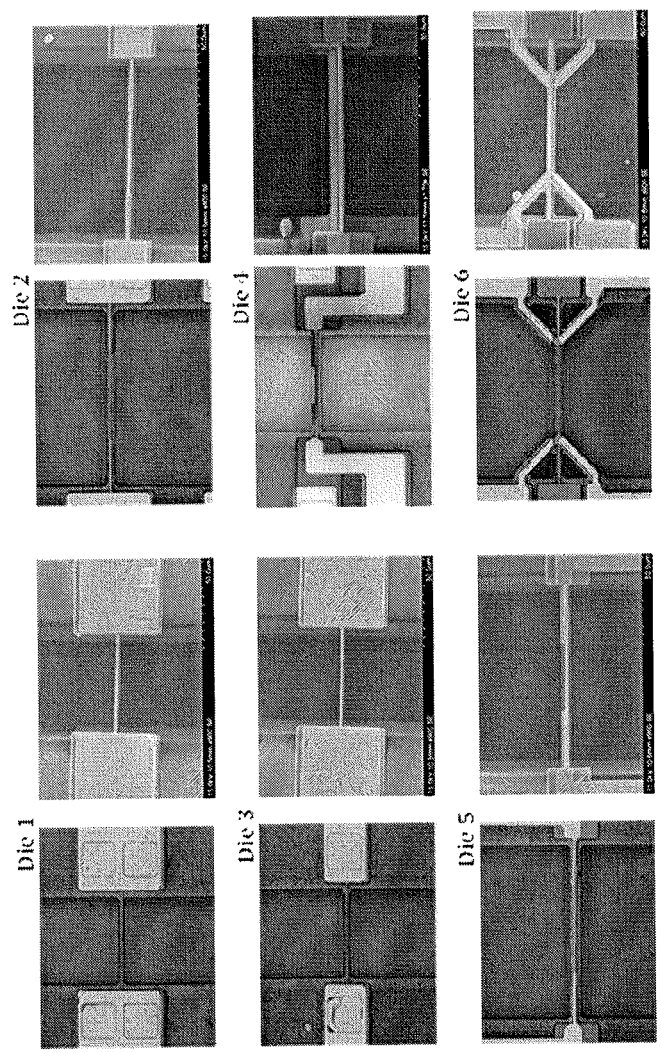
Figure 16: Optical and SEM images of the different exemplary sensor designs from second process wafer.

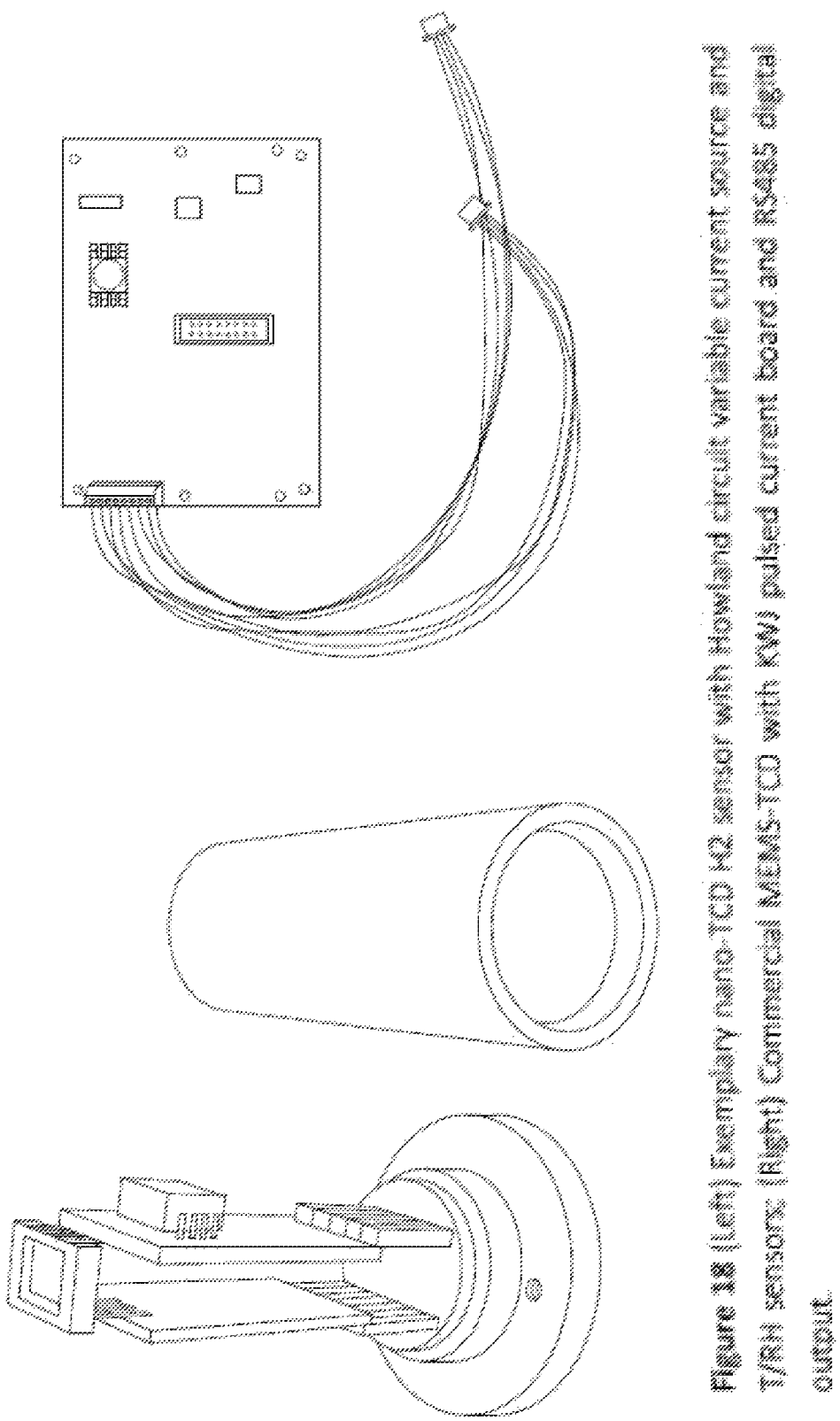
Figure 18 (Left) Exemplary nano-TCO kΩ sensor with Howland circuit variable current source and T/RH sensors (Right) Commercial MEMS-TCO with KWJ pulsed current board and RS485 digital output.

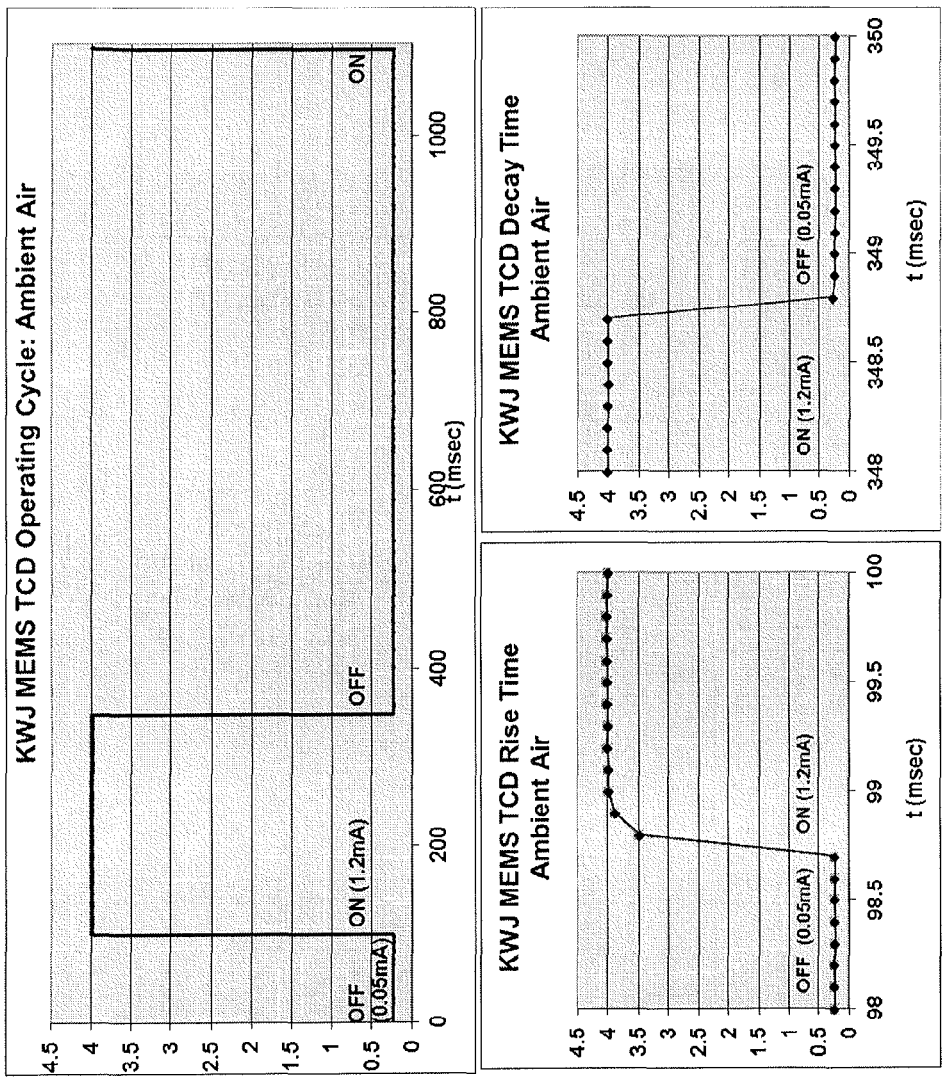
Figure 19 (Top) – One complete cycle, sensor powered for 250msec, and off for 750 msec
(Bottom) – same data, zoomed in on rise (left) and fall (right). Stabilization time of the sensor is clearly less than <0.3 msec, other data collected on 100MHz oscilloscope indicates sensor Figure 20: Response of KWJ "nanoTCD" vs commercial MEMS TCD to mixtures of 0-2.5% $H_2$.
a. Commercial MEMS TCD
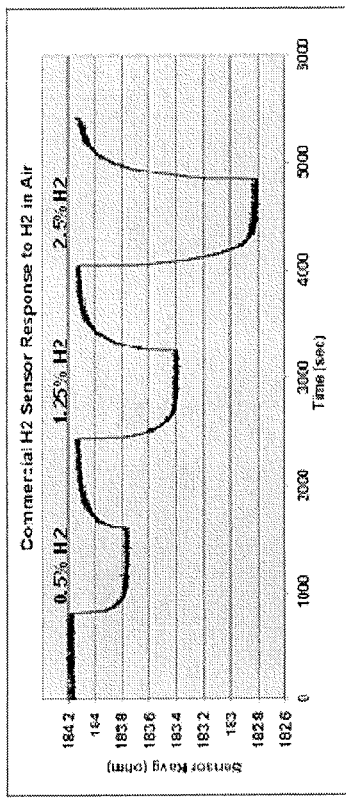
b. KWJ TCD sensor
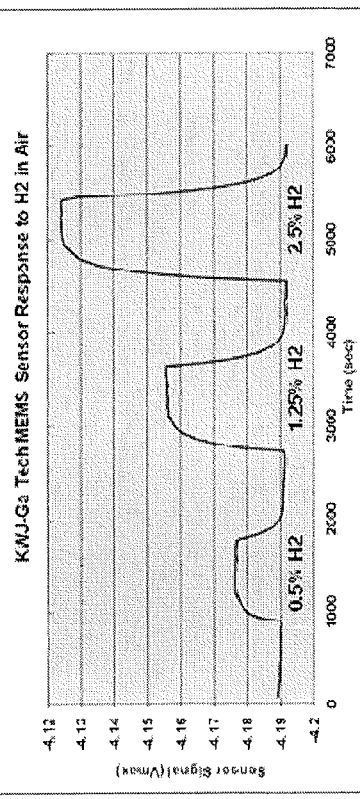
c. Temperature drift during time of this test
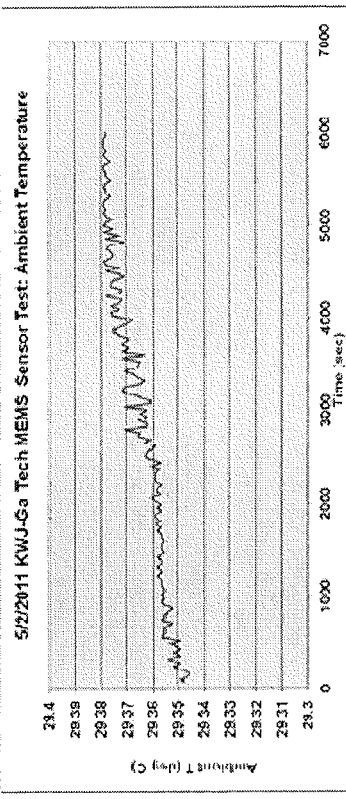

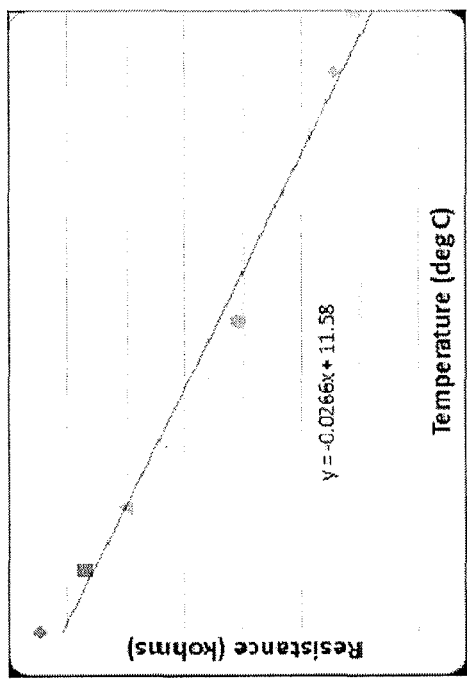
Figure 21: Typical R vs T curve for doped Polysilicon bridge.

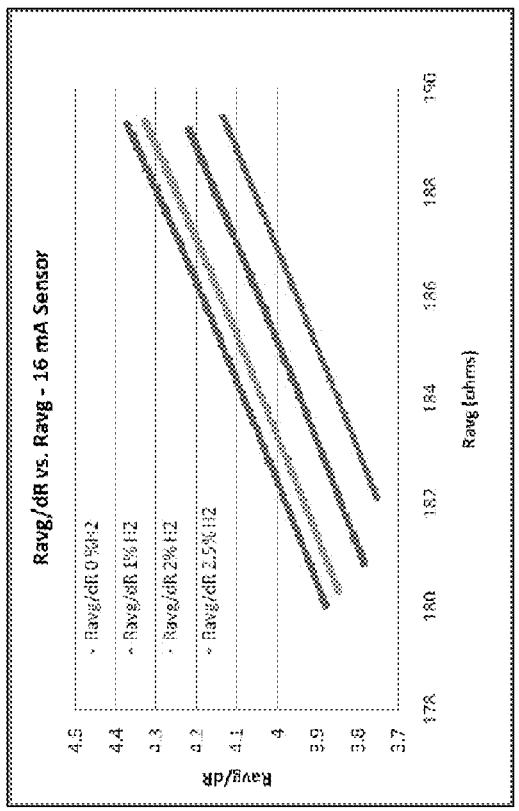
Figure 22a: 16 mA sensor plot for $R_{avg}/dR$ vs. $R_{avg}$ for
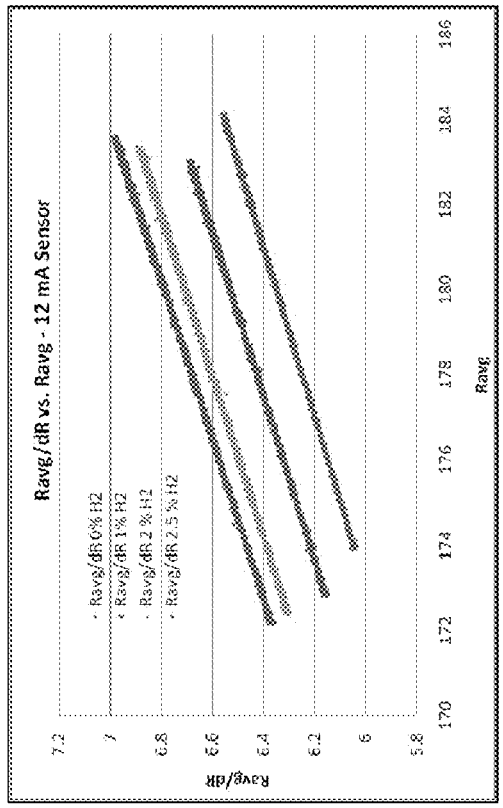
Figure 22b: 12 mA sensor plot for $R_{avg}/dR$ vs. $R_{avg}$ for

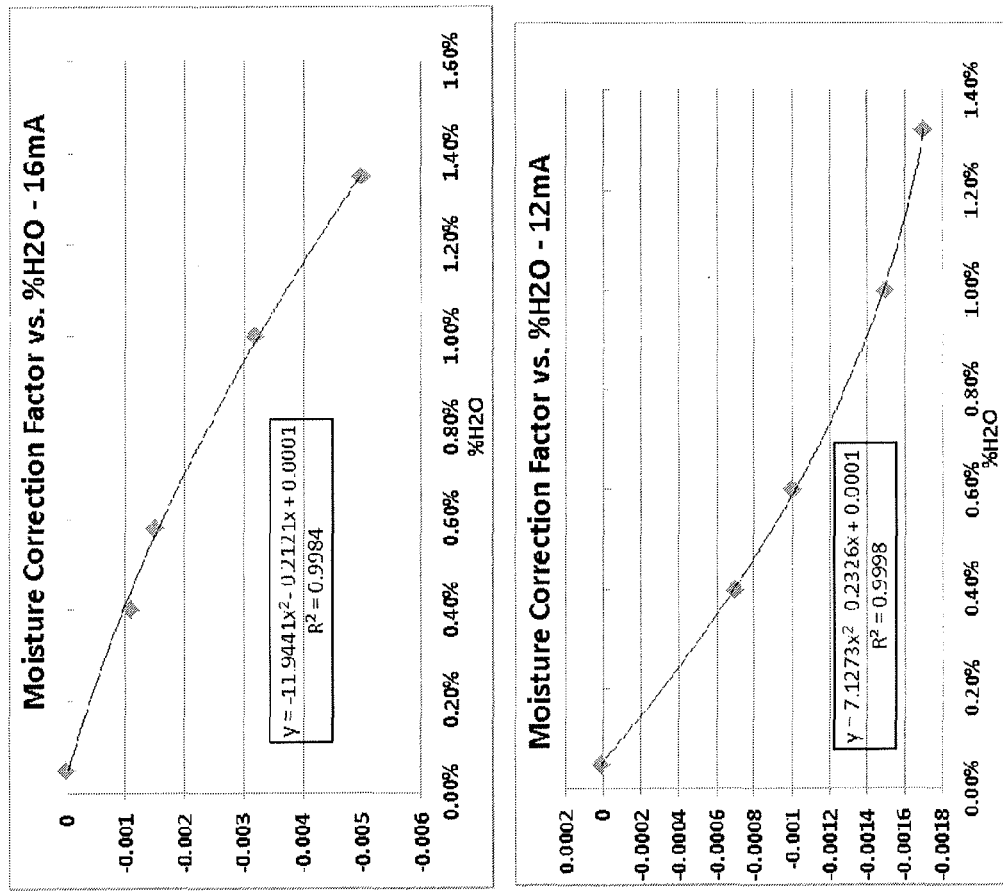
Figure 23: Plots of offset vs. %H$_2$O in sample. Top curve is for the 16 mA sensor, bottom for the 12 mA sensor.

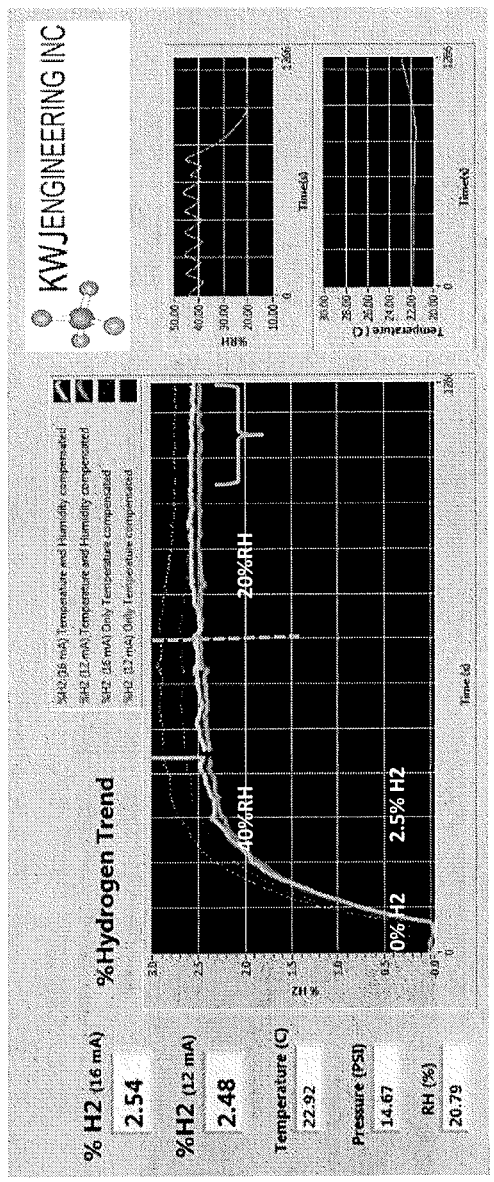
Figure 24: Screenshot of LabView GUI showing response of sensor to 2.5% H2 as the RH is varied from 40% to 20%, and T is raised from 20 to 25deg C.

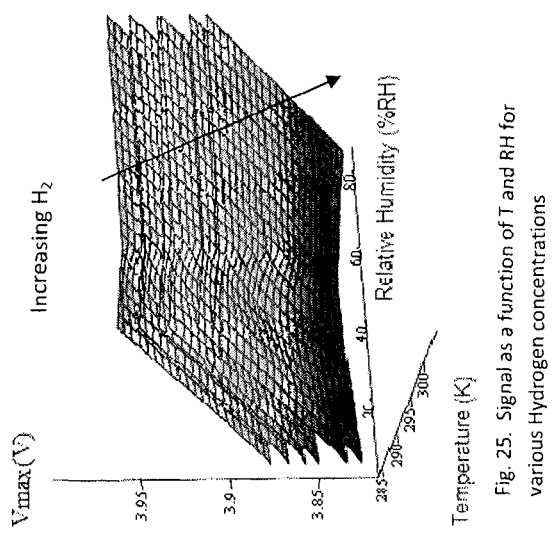
Fig. 25. Signal as a function of T and RH for various Hydrogen concentrations

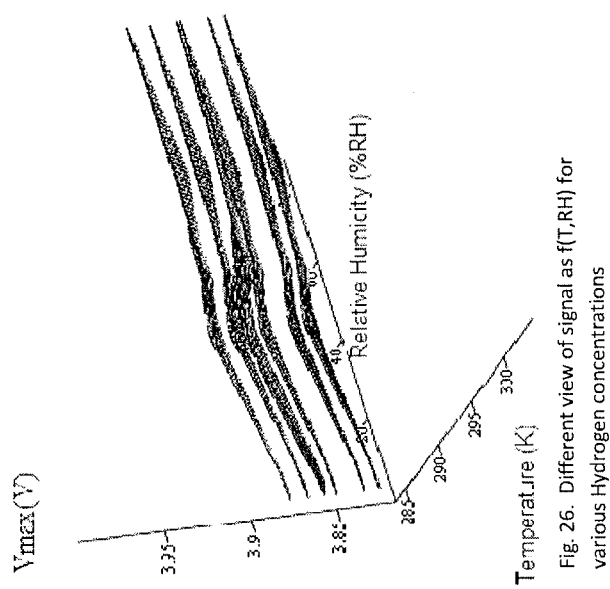
Fig. 26. Different view of signal as f(T,RH) for various Hydrogen concentrations

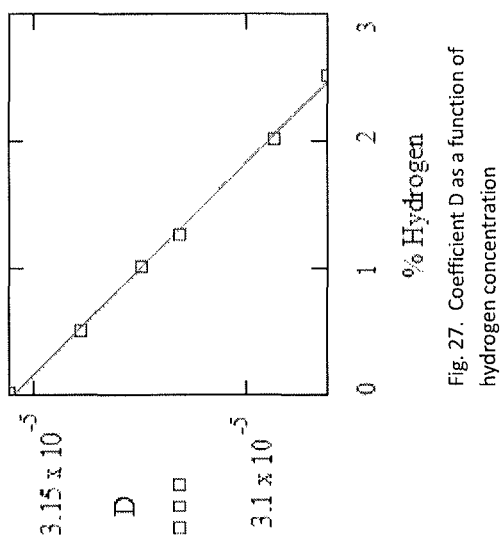
Fig. 27. Coefficient D as a function of hydrogen concentration

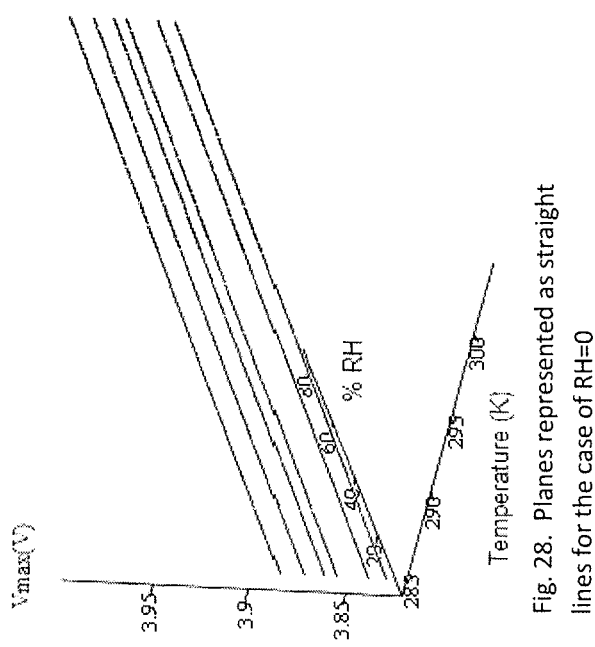
Fig. 28. Planes represented as straight lines for the case of RH=0

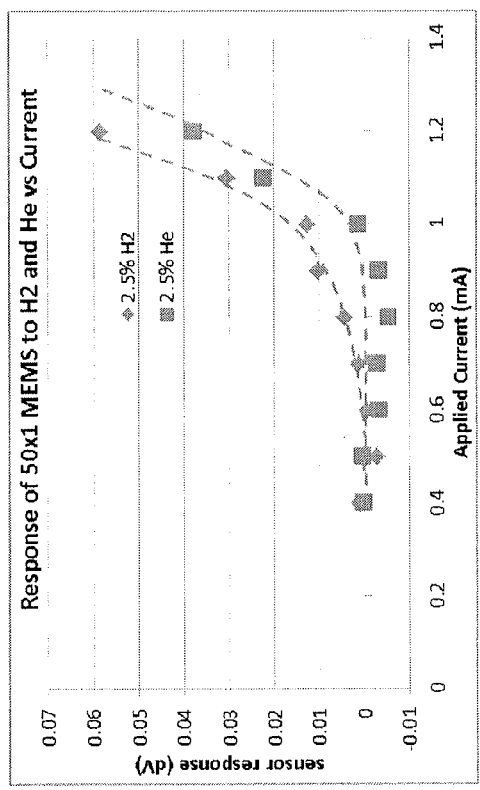
Figure 29: plot of d(Vmax) for 2.5% H2 vs air and 2.5% He vs. air. Note that H2 exhibits a response at 0.7 mA, while He shows no response below 1.0mA

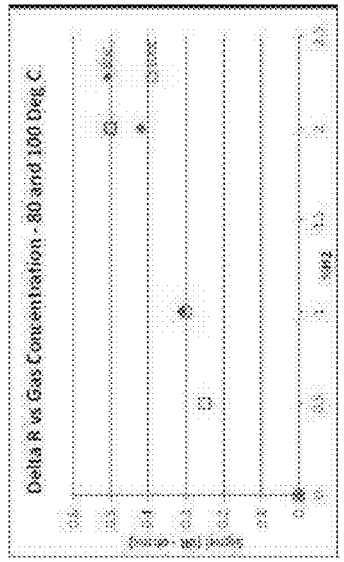
Figure 31: Response of the Pd nanoH$_2$ sensor to 0-2% H$_2$ at 80 and 100 deg C
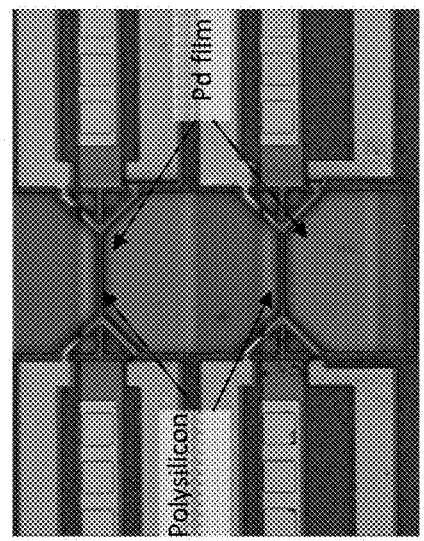
Figure 30. Optical photograph of Die 6, with a Pd film coating across the bridges (visible as light brown rectangles across the trench.)

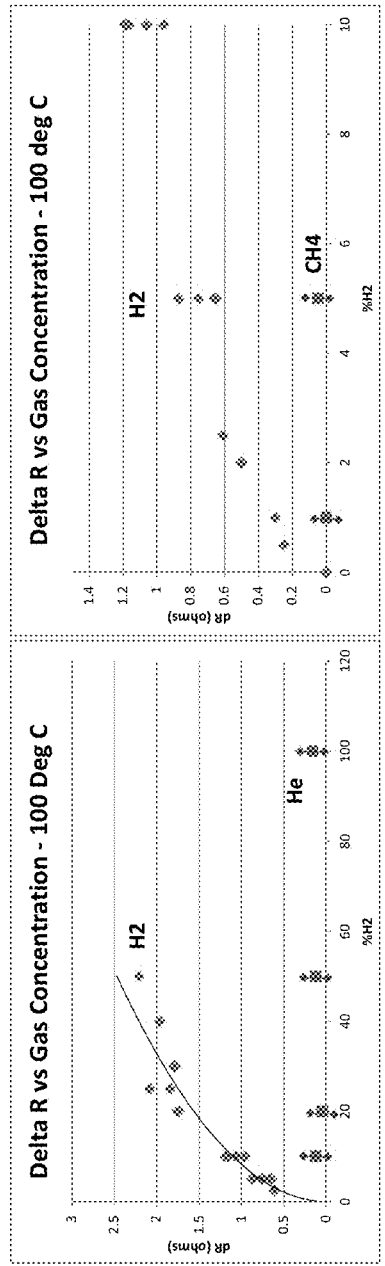
Figure 32.a (left): the response to 0-100% Helium relative to 0-50% $H_2$, Figure 32.b. (right): the response of 0-5% $CH_4$ relative to 010% $H_2$.

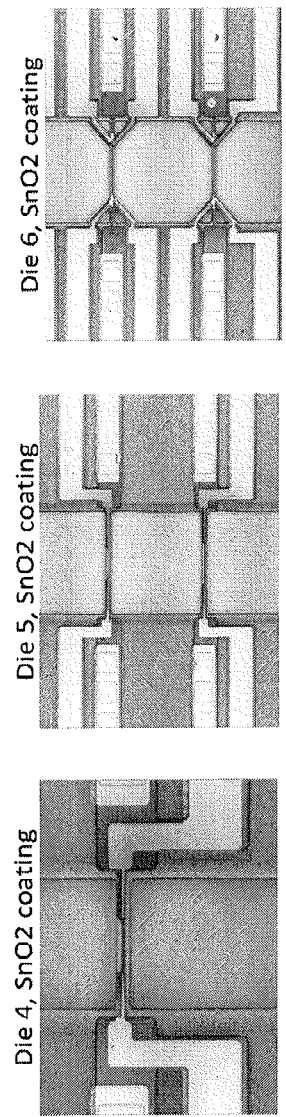
Figure 33: examples of Die 4, 5, and 6; with the SnO$_2$ coating

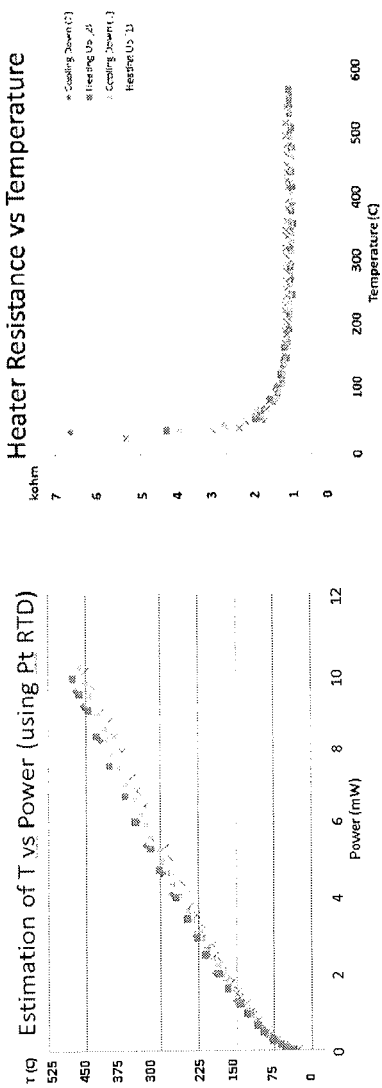
Figure 34: Plot of sensor temperature vs applied power (left) and polysilicon bridge resistance as a function of temperature (right) over two heating and cooling cycles. Sensor: Wafer 1, Die 5.

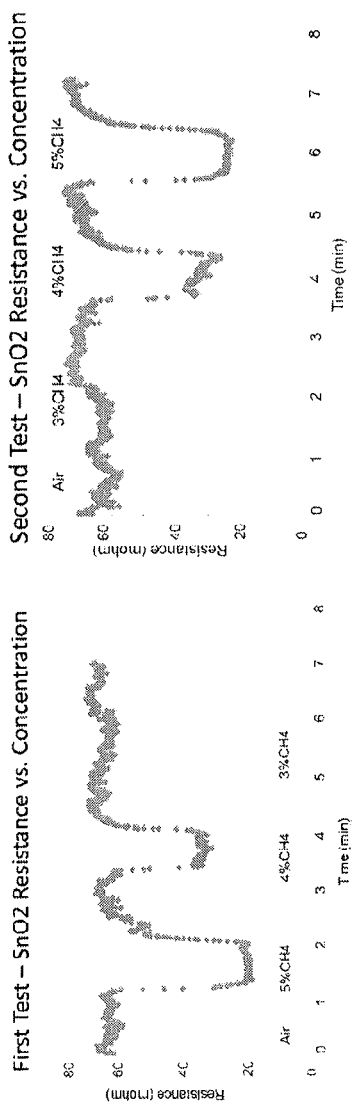
Figure 35: Plot of SnO$_2$ sensor resistance with different CH4 concentrations, two separate tests.. Sensor: Wafer 2, Die 4.

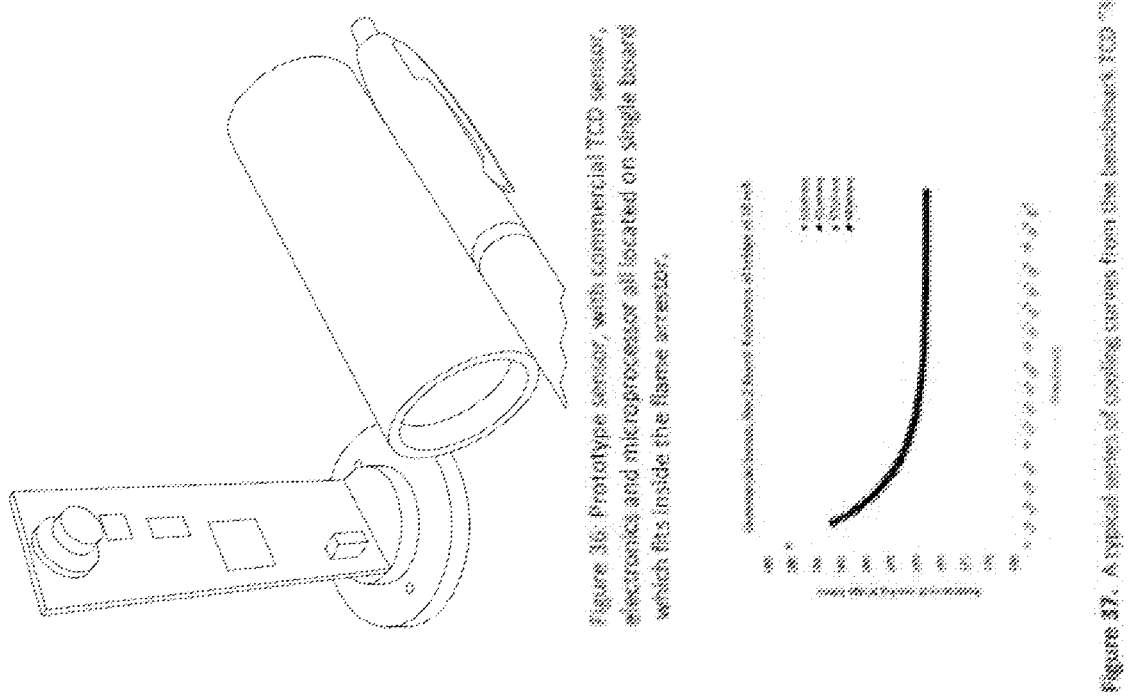

MULTI-DIMENSIONAL SENSORS AND SENSING SYSTEMS

CROSS-REFERENCE TO RELATED APPLICATIONS

This application is a continuation-in-part application of U.S. Non-Provisional patent application Ser. No. 13/271,659, filed Oct. 12, 2011, now granted as U.S. Pat. No. 8,426,932, which is a continuation-in-part application of U.S. Non-Provisional patent application Ser. No. 12/615,110, filed Nov. 9, 2009, now granted as U.S. Pat. No. 8,310,016, which is a continuation-in-part application of U.S. Non-Provisional patent application Ser. No. 11/879,462, filed Jul. 17, 2007, now granted as U.S. Pat. No. 7,911,010, the entire disclosures of which are hereby incorporated by reference herein. This application also claims priority from U.S. Provisional Patent Application Ser. No. 61/112,237, filed Nov. 7, 2008, and U.S. Provisional Patent Application Ser. No. 61/392,217, filed Oct. 12, 2010, the entire disclosures of which are hereby incorporated by reference herein.

STATEMENT REGARDING FEDERALLY SPONSORED RESEARCH OR DEVELOPMENT

This invention was made with government support under Contract NNX11OE36P awarded by NASA. The Government has certain rights in the invention.

TECHNICAL FIELD OF THE INVENTION

The present invention is directed to microfabricated devices and methods for making them, and more specifically, to a unique apparatus and method for making multiple kinds of sensors on a single platform. Specifically, the present invention is directed to sensors that are tiny and ultra low power as well as low cost, but sensitive to a variety of important chemical and physical parameters and can be used with unique operating protocols and interpretive algorithms to enable smart sensors.

BACKGROUND OF THE INVENTION

Recently there has been renewed interest in sustaining economic growth through utilization of fossil energy resources, such as coal, in an efficient and environmentally responsible manner. Advanced technology for power plants and gasifiers is important for the clean production of electric power, hydrogen generation, gasification of methane, production of industrial chemicals, refined fuels with reduced impact on water resources, solid waste disposal and capture of carbon dioxide generated in the use of fossil fuels. To meet the demand of future energy innovation, these industrial gases will be produced by clean processes. Sensors and controls are important ingredients in any modern process plant and the coal utilization plants will not be different. The development of effective sensors is vital, and such important technology must be available when needed so there is an effective process and rapid public acceptance of fossil energy utilization. Sensors will not only enable the clean, efficient, and low-cost process, but will also provide for safety in the workplace, home and environment. There is a need for sensors to be located as close to the process points as possible for control of the processes. In addition, there is a need for sensors at exit gas streams that feed auxiliary processes for clean-up or conditioning. Moreover, safety sensors in the plant, the surrounding environment and public spaces would help accelerate public acceptability and the pace of coal technology utilization. Safety sensors may also be utilized for medical and health reasons, especially sensors worn by an individual that may provide immediate feedback on the individual's health and safety. The requirements for such sensors typically exceed the capabilities of current sensors. Several major limitations for current process sensors include: potential severe conditions in and near process streams, interferences of the complex process stream components and the desired analytical measurement, slow response times for analytical information, the need for very low operational power requirements making the sensors incompatible with modern wireless systems, and especially the cost of deployment and ownership. Similarly, safety and environmental sensors are typically too costly and lack performance for easy, wide-spread deployment. So not only do sensors need to be cost effective for widespread deployment, but they also have to be simultaneously low power and tiny so they can be easily interfaced to process, safety, health, and environmental systems with and without wireless and other communication interfaces.

One recent innovation in the manufacturing of devices is microelectromechanical systems (MEMS) technology. MEMS technology is based on a number of tools and methodologies, which are used to form small structures with dimensions in the micrometer scale (one-millionth of a meter). Significant parts of the technology have been adopted from integrated circuit (IC) technology. For example, almost all devices are built on wafers of silicon like IC's. The structures are realized in thin films of materials and patterns using photolithographic methods. There are three basic building blocks in MEMS technology: 1) deposit thin films of material on a substrate, 2) apply a pattern mask on top of the films by photolithographic imaging, and 3) etching the film selectively in the mask. A MEMS process is usually a structured sequence of these operations to form actual devices and patterns can be made by either etching or lift off methods.

One of the most basic building blocks of MEMS processing is the ability to deposit thin films of materials that have different properties like insulators, semiconductors, conductors or special reactivity. The thin films can have a thickness anywhere from a few nanometers to several hundred micrometers. Films can subsequently be locally etched or lifted off to form patterns in the MEMS processes some of which are described below.

MEMS deposition technology can be classified into two groups called 1) depositions that happened because of a chemical reaction, such as chemical vapor deposition (CVD), electro deposition, epitaxy, and thermal oxidation; or 2) depositions that occur because of a physical reaction: such as physical vapor deposition (PVD) or casting. The chemical reaction processes exploit the creation or removal of solid materials directly from the surface by chemical reactions and gas and/or liquid interactions with the substrate material. The solid material is usually not the only product formed by the reaction. By-products can include gases, liquids or even other solids. The physical deposition processes have in common that the material deposited is physically moved onto the substrate. In other words, there is no chemical reaction which forms the material on the substrate. In the chemical reaction, a film or deposits can be made by electrodeposition or by thermal reaction of a gas with a hot substrate which are chemical reactions.

Lithography in the MEMS context is typically the transfer of a pattern to a photosensitive material by selective exposure to a radiation source such as light. Photosensitive materials are materials that experience a change in physical properties when exposed to a radiation source. If we selectively expose a photosensitive material to radiation (e.g. by masking some of the radiation), the pattern of the radiation on the materials is transferred to the photosensitive material exposed, as the properties of the exposed and unexposed regions differ. The washing of the unreacted materials leaves behind the patterned material in the desired pattern dictated by the mask. Subsequent depositions allow the layer to contact only the desired portions of the surface and subsequent removal of the photosensitive material allows the patterning of the deposited layer.

In order to form a functional MEMS structure on a substrate, it is necessary to etch the thin films previously deposited and/or the substrate itself. In general, there are two classes of etching processes: 1) wet etching where the material is dissolved when immersed in a chemical solution, or 2) dry etching where the material is sputtered or dissolved using reactive ions or a vapor phase etchant. As one skilled in the art will appreciate, advances in MEMS processing are ongoing and atomic layer deposition, plasma etching, and deep reactive ion etching and such techniques are constantly being advanced and developed to aid in the manufacture of tiny MEMS structures. There is a need within NASA and elsewhere in the gas detection community for low power gas sensors for analytical and safety applications on the ground and on board manned and unmanned vehicles and vessels. Critical gas analytes must be measured to ensure proper function of the on-board equipment and processes, and to ensure the safety of the crew on the ground and in flight. NASA applications include unique ground operations and remote travel. In such environments, power, size and weight are at a premium and resources are limited. Also, carrying spares, maintenance items and calibration equipment or consumables is undesirable. This means that the successful sensor must be stable and not require spare parts for calibrations for many years. Specifically, there is a need for an ultra-low power, high performance gas sensor platform capable of measuring He, $H_2$ and other gases in air and process streams on the ground and in space that is stable for years. There are of course these benefits in many other commercial and consumer applications like cell phones.

It is the desire herein for the development of a unique approach to generate a MEMS sensor platform with widespread applicability with advanced analytical capability and significant commercial potential. As such, there is a need for apparatuses and new methods for microfabricating multi-dimensional nano-sensor platforms. Accordingly, improved apparatus and methods for using the same are desired. Since MEMS processing has the largest applicability and advantage for large applications and not all chemical sensors applications are large, MEMS is not typically applied to the development of many kinds of chemical sensors. Therefore to achieve commercial viability for the MEMS processes with many chemical sensors, it is advantageous to have many sensors capable of being built on the same MEMS platform made with common MEMS processes. In addition to the versatility of the individual MEMS structure, multiple structures on the same die will result in both redundancy for higher reliability and long lifetime as well as each area functionalized differently providing orthogonally responding devices on the same platform. While building tiny MEMS sensors can be achieved, many of the smallest structures can lack stability or corrode or degrade in performance rapidly especially when operated at elevated temperatures and in real environments. Accordingly, there is also a continuing need for a device that it is stable for long lifetimes and yet is still very small and low power in operation.

SUMMARY OF THE INVENTION

The present invention relates to monitoring devices that include a power source, wireless communication equipment, and at least one sensor or sensing system utilizing microelectromechanical systems (MEMS) technology that consumes less than 500 µW of power. The power can be continuous or intermittent and measured as an average power consumed over the sensor lifetime. Data gathered from the at least one sensor or sensing system by using novel operating modes and interpretive algorithms is transferred by the wireless communication equipment to a central communication hub or to a wired or wireless system appropriate to the application.

The present exemplary nano-sensor platform addresses multiple sensing applications with its MEMS multi-element sensing chip which we call the MMSMS chip [the Multi-element Multi-functional Smart Mems Sensor chip or the MMSMS chip].

Another aspect of the invention relates to a method of monitoring personnel by using a monitoring device that includes a power source, wireless communication equipment, and at least one sensor or sensing system utilizing MEMS technology that consumes less than 500 µW of power. Data gathered from the at least one sensor or sensing system is transferred by the wireless communication equipment to a central communication hub or appropriate communications system and/or subsystem. In these applications, easily wearable sensing devices are needed and such capability is enabled by the tiny MEMS sensors, and low power which obviates the need for a small battery or lack of battery, instead utilizing alternatives like power scavenger or power harvester subsystems.

Another aspect of the invention relates to methods and apparatus for microfabricating multi-dimensional multi-use versatile sensor platforms, such as sensor platforms with multiple structures that can sense several simultaneously needed chemical, biochemical or physical variables. One aspect of the invention is a universal microelectromechanical nano-sensor platform. The platform comprises a substrate having a surface with a first insulating surface layer; a microstructure first conductive layer deposited in one or more patterns on the surface to make several elements or devices; a second insulation layer, wherein the insulation layer is configured such that it covers at least some portion of the first conductive layer's one or more patterns; a second conductive layer deposited in one or more patterns to form electrodes, wherein the elements or device can be utilized for sensing; and one or more functionalization layers deposited on at least some portion of the second conductive layer, wherein the functionalization layers are adapted to provide one or more transducer sensor classes selected from the group consisting of: radiant, electrochemical, electronic, chemical, magnetic and thermal class of chemical sensors. The many variants of chemical sensors and applications can give rise to many materials and methods used in construction, examples of which may be found in "*Experimental Methods in Chemical Sensor and Sensor Array Evaluation and Development*," Chapter 1 in *Materials and Sensor Arrays—Computational and Experimental Selection Methods*, M. A. Ryan, J. R. Stetter, et al., editors, [Book: Joseph R. Stetter, Chapter 1, *"Experimental Methods in Chemical Sensor and Sensor Array Evaluation and Development*," in "Computational Methods for Sensor Materials Selection, M. A. Ryan, A. V. Shevade, C. J. Taylor, M. L. Homer, M. Blanco, and J. R. Stetter, editors, 2009, pp 3-46. DOI 10.1007/978-0-387-73715-7-1 Copyright Springer Science+Business Media, LLC 2009. ISBN978-0-387-73714-0 (Series INTEGRATED ANAL. SYSTEMS, R. A. Potyrailo, ed.)] and also [R. J. Aguilar, Zhengchun Peng, P. J. Hesketh; and J. R. Stetter, Ultra-Low Power Microbridge Gas Sensor; *Proceedings of the 218th Meeting of the Electrochemical Society*; Transactions of the Electrochemical Society, 33(8), 245-253 2010; Chemical Sensors 9 and MEMs/NEMS 9, October 2010, Hunter, Hesketh, et al., eds., Pub. By The Electrochemical Society, Pennington, N.J. 08534 ISBN978-156677-827-5. R. Aguilar, Z. Peng, P. J. Hesketh J. R. Stetter, "An Ultra-Low Power Microbridge Gas Sensor," Electrochem. Soc. Trans., 33 (8), 245-253 (2010).], the entire discloures of which are incorporated herein. However, not all combinations of the materials and processes result in an element or device which possesses the surprising combined properties of sensor performance for practical application in modern low power low cost situations and applications. And not all devices can implement the unique operating protocols and smart algorithms that enable automated temperature correction or multigas compositional analysis as does this structure. And not all sensors of the TCD or chemiresistor type have sufficiently low power to work effectively with modern wireless electronics, cellphones, or energy harvesting circuits that are used in many field applications.

Another aspect of the invention is a universal microelectromechanical nano-sensor platform. In this embodiment, the nano-sensor platform comprises: a semiconductor substrate including an upper surface, wherein the upper surface comprises an insulator or has an insulator layer thereon; a microstructure conductive layer deposited in a pattern on the surface to make several devices, wherein the conductive layer comprises one ore more filaments, bridges or filament pairs, and wherein the filaments are disposed above and parallel to the substrate configured such that there is an air gap between the filaments and the upper surface of the substrate; wherein the filaments comprise a size/width of less than 10 microns and a thickness of 1 micron or less. In practice, it is often convenient to construct such filament structures such that they exist in the plane of the surface and are undercut to provide a gap between the structure and the surface.

Another aspect of the invention is a universal microelectromechanical nano-sensor platform. The nano-sensor platform comprises: a semiconductor substrate including a surface; a microstructure polysilicon layer deposited in a pattern on the surface to make several devices, wherein the polysilicon layer comprises a first pair of filaments, wherein the filaments are disposed above and parallel to the semiconductor substrate with an air gap between the base of the filaments and the surface of the substrate; an insulation layer, wherein the insulation layer is configured such that the first pair of filaments of the polysilicon layer remain exposed and are not covered by the insulation layer; one or more functionalization layers deposited on the exposed pair of filaments of the polysilicon layer, wherein the one or more functionalization layers are adapted to provide one or more transducer platform classes selected from the group consisting of: radiant, electrochemical, electronic, mechanical and thermal; and wherein at least one pair of the filaments have a width of less than 10 microns. The small size allows a very rapid response measured in nano-seconds that has heretofore not been observed in such chemical sensors as well as simultaneously being of a low power of operation measured in nano-Watts that was heretofore not possible. The specific design used here and the specific characteristics of the layer of materials and their method of fabrication have further allowed a high level of reliability (e.g., layers are put together with the proper stresses and tensions and materials and procedures so as to allow the fabrication of a rugged structure even though the structures are very small). This reliability has been measured exceeding tens of billions of measurement cycles without any significant drift in electronic properties. This has been an issue with other devices in that as they are made smaller, many new types of failure modes cause short lifetimes because of the delamination of layers or corrosion or otherwise degraded structures that lack the stability or the long term lifetime that is important to analytical devices. Therefore, it is desirable that the active element (polysilicon suspended element) be encapsulated by the defect free insulation layers to mitigate degradation with use over time at both low and elevated temperatures and in differing chemical and physical environments.

The apparatus and methods for manufacturing nano-sensor platforms are advantageous for environmental, health, process, and safety monitoring of fluids, especially small molecule gases. It can now be seen that the many different functionalization layers of the same MEMS platform provides for an almost boundless number of sensors and sensor arrays that contain homogenous and/or heterogeneous layers on the exact same MEMS prepared platform with a wide variety of sensing reactions and reactivity. Not only can many sensors be arrayed on a single surface but the present invention allows diverse and different classes of sensors and related devices like preconcentrators to be prepared on the same substrate with no change to the underlying platform but only a change in the selection of the functionalization layer(s) in the final processing steps. The surprising number of orthogonally reactive sensors and sensor classes on the same platform constitute a new and more powerful sensing capability. In addition to the surprisingly more effective sensing, the new platform allows designs that are ultra low power for portability, versatility, and interface with modern wireless systems for the underlying platform [e.g., leading to potentially higher production volumes] making MEMS fabrication of chemical sensors practical for real-world applications that are low volume, while heretofore only high volume applications were economically possible and commercially viable using MEMS. There are many additional couplings of this technology to the world of sensing such as thermal isolation techniques to achieve lower power, the use of the ever increasing number of possible materials including plastics and composites, flexible circuit materials for construction, and alternative selective and non-selective functionalization layers for use in liquids and gases. Some surprising advantages include the ability to realize simultaneously, the low power, tiny size, high volume, MEMS fabricated devices in a very reliable design and structure that has versatility heretofore not realized. Further, when applied to practical problems, the speed of response, unique operating modes that are steady state and/or time-power dependent, as well as novel interpretive algorithms, enable the sensors to provide outputs that are physically and chemically compensated for more accurate and reliable sensing in real-world applications. These and additional advantages will be apparent in view of the detailed description.

One embodiment of the present application is a novel ultra-low power MEMS sensor platform capable of measurement of important gases in safety, health, process and environmental monitoring applications at NASA and other medical, industrial, and consumer markets. The present exemplary MEMS sensors exhibit extremely long lifetime and MTBF [mean time between failure]. These exemplary designs are exceptionally rugged to survive ground, launch, and stress. One exemplary nano-TCD (Thermal Conductivity Detector) structure has survived billions of measurement cycles without significant drift in signal or degradation of response and require little if any maintenance or consumable supplies. The small mass and low surface area produces extremely fast thermal time constants, measured in nano-seconds, enabling versatile fast data gathering with broad interpretive power on nanoWatts of power.

In other exemplary embodiments, smart materials are integrated onto the thermal sensor element and can provide chemically selective responses based upon well-established physics and chemistry. The speed and low power of the detector allow this selectivity information to be obtained and interpreted in real-time measurements of gases.

Exemplary smart operational protocol and smart algorithm are discussed in the following paragraph. If we operate the sensing element as a TCD and in a time-dependent signal mode, i.e. where the signal [or property of the sensor such as resistance] is measured over time as the power to the sensor or other influential variable on the signal is changed, then the resulting time dependent data file has information about the gas(es) being sensed and the environmental conditions. One possible variation is to measure the decay curve when the element is turned off or to measure the signal [e.g., resistance] at the hot temperature and at the cold temperature multiple times at multiple temperatures. We have found from calibration curves that there is only one non-variant over time resistance of the element in a given gas [e.g. zero air] at a single temperature and power level. We can designate this, $C_{Tmeas,0}$ and this is found by calibration of the sensing element at various temperatures in zero air. During a measurement, using our novel smart measurement protocol, we obtain $C_{Tmeas,unk}$ and the analytical signal, i.e., the difference in C, or dC, with and without the target gas(es) present in the air is Analytical Signal=$[C_{Tmeas,unk}-C_{Tmeas,0}]$ at the temperature of the measurement and the value for $C_{Tmeas,0}$ is found form the calibration data. In the simplest model of the smart algorithm, the signal is generated at more than one operating temperatures [e.g., different power levels, voltages, or currents]. This can be accomplished rapidly, in microseconds because the sensing elements are very small, fast responding and very low power. Now that the signal is known at more than one measuring power or temperature, we can equate the signal to the concentration of the gas(es) in air. To a first approximation, the signal is the sum of the signal for the individual gas(es) present. Therefore, if we have differing H2 content and He content in air [to continue our example], the signal would be a composite of the two gases and can be expressed as $$[C_{Tmeas,unk}-C_{Tmeas,0}]=C'*[\% H2]+C''*[\% He] \quad \text{Eq.1.}$$

All values taken at the measured temperature. The constants C' and C'' are the calibration constants at the measured temperature for the gases H2 and He, respectively and are obtained from calibration curves for the sensor. The signal and the constants C' and C'' are uniquely dependent on the operating conditions selected [in this example we suggested operating at different power or temperatures]. Continuing our example, because we can write the Equation 1 at different conditions [different currents for example] and the constants C' and C'' will be unique under each set of conditions, we see that we will have two equation in two unknowns if we write this for two conditions and we can solve the equations uniquely for the concentration of more than both target gases, i.e. % H2 and % He, in our example. Now it will be obvious to one skilled in the art that any combination of gases with the unique set of parameter-dependent constants [the C', C'' being temperature dependent in our example] and any parameter that can be operationally varied, temperature, power, flow, etc., can create the information required to not only temperature correct the signal but also then, from multiple measurements in this parameter space, to determine multiple constituents. Also, non-linear and complex dependencies can be envisioned for more complex dependencies as can exist with certain concentrations and certain interactive gases. All that is required is that the number of variables and variability be appropriate to the problem. Selectivity can also be accomplished within this approach since, if the temperature dependence of the signals, dC, and the calibration constant, e.g. C' are identical, it means that the gas must only contain the gas that corresponds to the C' and no other species is present. Conversely, if the temperature dependence is different for the signal from the C', then there must be some other gas present, i.e., some C'' or a more complex situation. This situation can then be solved for each constituent if the constants are known through calibration. This is an example of the interpretive capability of this sensor when operated in a smart mode and interpreted using smart algorithms to improve sensitivity, selectivity, and analytical analysis capability for the singular element operated under variable operating conditions.

The present embodiments of the MEMS sensor have demonstrated characteristics of ultra-low power operation [<10 nanowatt per reading, >1000× lower than existing devices], fast response [measured in nanoseconds, >1000 times faster than current devices], stability [through billions of measurements and over environmental temperature and RH ranges, implying long calibration cycles i.e., >5 years], with no consumables and unprecedented selectivity. For example, in exemplary embodiments:

a µW-powered Pd film hydrogen sensor, operating at 100° C. (<1 mW continuous operation, <10 µW at 1% duty cycle) responds to <0.25% H2, but no measureable response to 100% He and >5% CH4.

Operation of multiple currents to discrimination between $H_2$ and He, with no response at up to at least 2.5% He (<5 µW with 1 msec/sec duty cycle). This sensor has no reactive coating, so is not subject to the drift and "poisoning" of HMOx and Pd films and is stable without calibration for >5 years. This selectivity is believed to be accomplished based on the exemplary MEMS structure, unique exemplary operating protocol and exemplary smart algorithm of the present application.

BRIEF DESCRIPTION OF THE DRAWINGS

While the specification concludes with claims particularly pointing out and distinctly claiming the invention, it is believed the same will be better understood from the following description taken in conjunction with the accompanying drawings in which:

FIG. 12 is a top view pattern of sensor platforms according to exemplary embodiments of the present invention.

FIG. 13 is a top view pattern of sensor platforms according to exemplary embodiments of the present invention.

FIG. 14 are top view patterns of sensor platforms according to exemplary embodiments of the present invention.

FIG. 15 illustrates processing of $SiO_2$ coated Si wafers to fabricate sensor platforms according to exemplary embodiments of the present invention.

FIG. 16 illustrates images of exemplary embodiments of sensor platforms of the present invention.

FIG. 18 illustrates images of exemplary embodiments of sensor platforms in circuits of the present invention.

FIG. 19 illustrates sensor response charts relating to exemplary embodiments of the present invention.

FIG. 20 illustrates sensor response charts relating to exemplary embodiments of the present invention.

FIG. 21 illustrates sensor response charts relating to exemplary embodiments of the present invention.

FIGS. 22a and 22b illustrate sensor response charts relating to exemplary embodiments of the present invention.

FIG. 23 illustrates sensor response charts relating to exemplary embodiments of the present invention.

FIG. 24 illustrates sensor response charts relating to exemplary embodiments of the present invention.

FIG. 25 illustrates sensor response charts relating to exemplary embodiments of the present invention.

FIG. 26 illustrates sensor response charts relating to exemplary embodiments of the present invention.

FIG. 27 illustrates sensor response charts relating to exemplary embodiments of the present invention.

FIG. 28 illustrates sensor response charts relating to exemplary embodiments of the present invention.

FIG. 29 illustrates sensor response charts relating to exemplary embodiments of the present invention.

FIG. 30 illustrates images of exemplary embodiments of sensor platforms of the present invention.

FIG. 31 illustrates sensor response charts relating to exemplary embodiments of the present invention.

FIGS. 32a and 32b illustrate sensor response charts relating to exemplary embodiments of the present invention.

FIG. 33 illustrates images of exemplary embodiments of sensor platforms of the present invention.

FIG. 34 illustrates sensor response charts relating to exemplary embodiments of the present invention.

FIG. 35 illustrates sensor response charts relating to exemplary embodiments of the present invention.

FIG. 36 illustrates images of exemplary embodiments of sensor platforms of the present invention.

FIG. 37 illustrates sensor response charts relating to exemplary embodiments of the present invention.

Figure 1:
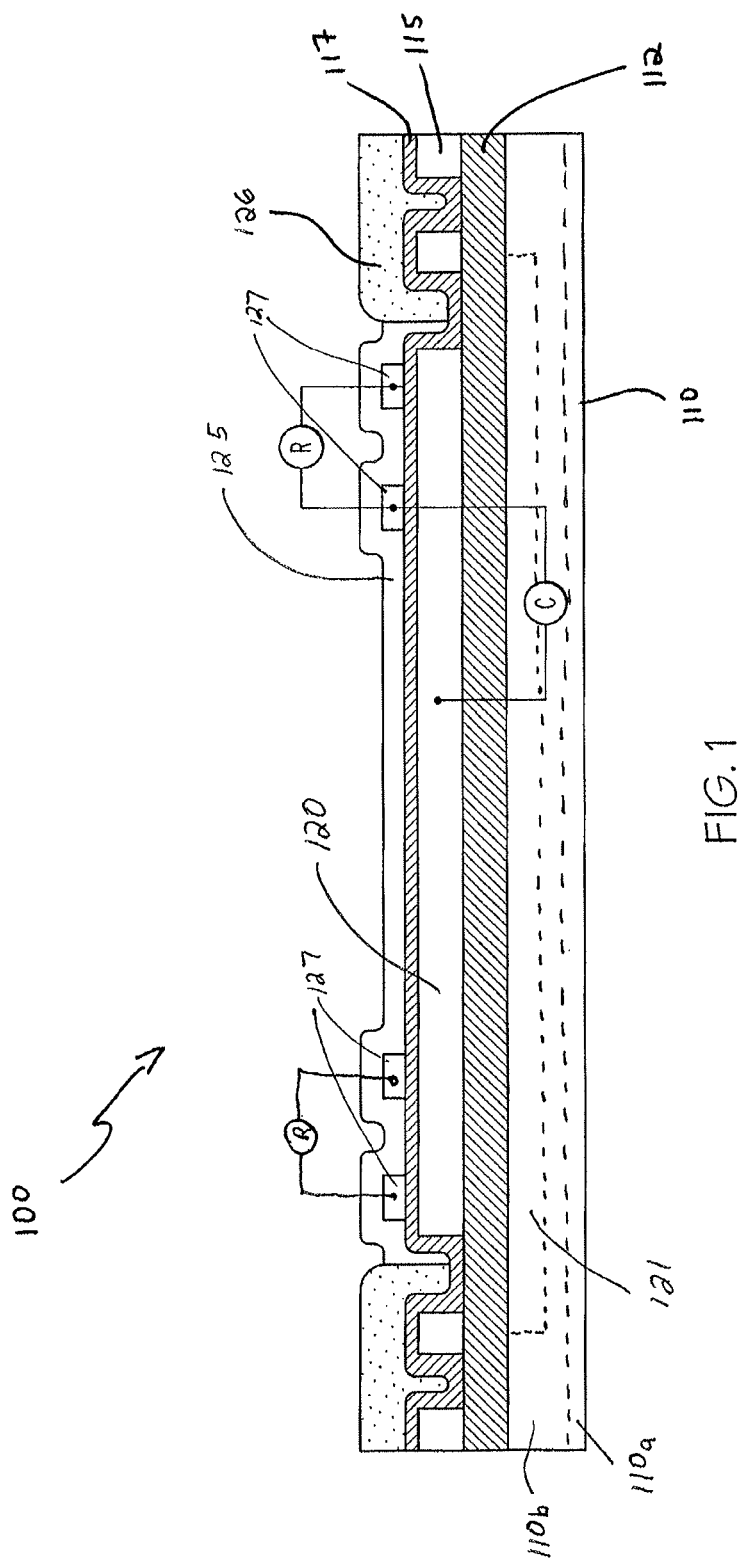
FIG. 1 is a cross-sectional illustration of a microelectromechanical sensor platform according to an exemplary embodiment of the present invention.

The embodiments set forth in the drawings are illustrative in nature, and not intended to be limiting of the invention defined by the claims. Moreover, the individual features of the drawings and the invention will be more fully apparent and understood in view of the detailed description.

DETAILED DESCRIPTION OF THE INVENTION

Reference will now be made in detail to various embodiments which are illustrated in the accompanying drawings, wherein like numerals indicate similar elements throughout the views.

One embodiment of the present invention is the development of microfabricated sensors that can detect critical fluids, especially small molecule gases. Putting this technology into a low-cost MEMS package can add to the unique character of the resulting sensors. These MEMS sensors will be unique because of the combination of high-technological performance, tiny size, low power and low cost and the potential for long lifetime and exceptional stability (which is unique for chemical sensors and significantly increases the ability of these chemical sensors to be part of modern wired and wireless sensing systems).

Described below in varying embodiments are unobtrusive, small, lightweight and energy efficient monitoring devices combining communication equipment and various sensors for detection of important and hazardous gasses, surrounding environmental conditions and personnel vital signs. This unique set of parameters is important for monitoring in many situations including emergency response to fires in civilian and military situations. At least one monitoring device is wirelessly connected to a central communication hub, allowing communication of various data between the at least one monitoring device and the central communication hub. Because embodiments of the monitoring device are small, lightweight and low power, they may be utilized in various fashions or incorporated into various equipments. Non-limiting examples include, but are not limited to, mounting the monitoring device on or within an earpiece, wearing the device on the body of personnel or integration of the device into various personnel clothing or equipment.

Embodiments of the monitoring device may incorporate any unobtrusive, small, lightweight and energy efficient communication equipment, as the particular variety of communication equipment is not vital to the invention. Communication between the monitoring device(s) and the central communication hub may integrate any feasible types of communication, including, but not limited to, radio frequency signal transmission, satellite transmission, any various voice communication channels and combinations thereof. One particular non-limiting embodiment utilizes cellular phone communication. Communication may be carried out in a one-way fashion from either a monitoring device to the central communication hub or vice versa, a two-way fashion allowing back and forth communication between a monitoring device and the central communication hub or in a fashion allowing open communication between multiple monitoring devices and the central communication hub.

Embodiments of the monitoring device may incorporate any unobtrusive, small, lightweight and energy efficient sensor that monitors personnel vital signs. Possible vital sign sensors include, but are not limited to, sensors that monitor heart rate, body temperature, respiration rate, blood pressure, pulse oximetry and any combination thereof. Vital sign sensors may contact the body of the personnel at various points including, but not limited to, the ear, ear canal, neck, chest, stomach, arm, wrist, leg and foot. Vital sign sensors may also be integrated into various personnel clothing or equipment, and thus in some embodiments, not contact the body of the personnel. For example, in certain non-limiting embodiments, a vital sign sensor monitoring personnel breathing rate may be incorporated into an oxygen mask.

Embodiments of the monitoring devices also may incorporate any unobtrusive, small, lightweight and energy efficient sensor that monitors hazardous gasses. Possible important and hazardous gas sensors include, but are not limited to, sensors that monitor oxygen, hydrogen, methane, carbon monoxide, hydrogen sulfide, chlorine, ozone, diesel particulates, gasoline fumes, ethanol and combinations thereof. Embodiments of the monitoring devices also may incorporate any unobtrusive, small, lightweight and energy efficient sensor that monitors surrounding environmental conditions. Possible surrounding environmental condition sensors include, but are not limited to, sensors that monitor temperature, pressure, radiation, moisture and combinations thereof.

One aspect of the invention is a universal microelectromechanical nano-sensor platform. The platform comprises a substrate having a surface with a first insulating surface layer; a microstructure first conductive layer deposited in one or more patterns on the surface to make several devices; a second insulation layer, wherein the insulation layer is configured such that it covers at least some portion of the first conductive layer's one or more patterns; a second conductive layer deposited in one or more patterns to form electrodes, wherein the device can be utilized for sensing; and one or more functionalization layers deposited on at least some portion of the second conductive layer, wherein the functionalization layers are adapted to provide one or more transducer sensor classes selected from the group consisting of: radiant, electrochemical, electronic, chemical, magnetic and thermal chemical sensors.

The sensing films (functionalization layers) can comprise electrolytes and then this sensor can function as an electrochemical sensor for CO, H2S, NOx, EtOH, or any suitable electroactive molecule. In an alternative embodiment, the sensing films (functionalization layers) can be polymers, selective adsorbents, composites, or other sensing materials such that the electronic sensor functions as a chemiresistor, chemicapacitor or an active device like a chemically sensitive transistor as the electronic properties of the functionalization layers are monitored as the target molecule interacts with the sensing film and the electrodes provide means to detect this interaction in an external circuit or recording means.

In one exemplary embodiment, the functionalization layers comprise metal oxide [MOX] materials like SnO2, ZnO2, WO3, and these inorganic coatings will make electronic sensors like chemiresistors to atmospheric gases of all kinds including O2, CO, H2S, NOx, hydrocarbons, H2, or the like. The MOX materials often can be operated at selected temperatures [0-750° C.] in order to adjust reactivity and the above structure allow this controlled operation with heaters and temperature sensors below the functionalization layers.

In another exemplary embodiment, the underlying heater and temperature sensors can be used to control the temperature of operation making the sensor functionalization layers more or less reactive to specific target analytes. In yet another embodiment, the thermal isolation of the active area [heater, temperature sensor, electrodes, functionalization layers] can allow low power operation and fast response and good T control for accurate sensing using temperature dependence of signals. In one exemplary embodiment, the elements are filaments or bridges that are designed to pass current and be heated but are also tiny enough structure to reach high temperatures and have very low power requirements. Also, the filament are capable of being heaters themselves as well as electrodes and can provide surfaces to make sensors that rely on constant or variable temperature control for operation and generation of useful sensing signals.

The Steinhart-Hart equation is a widely used third-order approximation for temperature dependence of resistance of semiconductors:

$$T = \frac{1}{a + b\ln R + c(\ln R)^3}$$

where a, b and c are called the Steinhart-Hart parameters, and must be specified for each device. T is the temperature in Kelvin's and R is the resistance in ohms. To give resistance as a function of temperature, the above can be rearranged into:

$$R = e^{(\beta - \frac{\alpha}{2})^{\frac{1}{3}} - (\beta + \frac{\alpha}{2})^{\frac{1}{3}}}$$

where $$\alpha = \frac{a - \frac{1}{T}}{c} \text{ and } \beta = \sqrt{\left(\frac{b}{3c}\right)^3 + \frac{\alpha^2}{4}}$$

The error in the Steinhart-Hart equation is generally less than 0.02° C. in the measurement of temperature. As an example, typical values for a thermistor with a resistance of 3000 ohms at room temperature (25° C.=298.15 K) are:
a=1.40×10$^{-3}$
b=2.37×10$^{-4}$
c=9.90×10$^{-8}$ More frequently for metals or alloys a first order equation approximated the coefficient of resistance where $(R-R_0)=k^*(T-T_{ref})$ that is dR=K dT where K is the coefficient of resistance and can be positive or negative. For metals like Pt, K can be 0.003 ohms per degree and a similar value for highly-doped polysilicon, and for metal oxides and low doped-polysilicon the TCR can be much larger and typical of semiconductors and thermistors. It can be an advantage to select materials and designs that are very stable and can operate in the desired temperature range and in the desired matrix [where the fluid is air or liquid]. The resistor can be coated to give it resistance to corrosion and provide other robustness.

In a further embodiment of the present invention, encapsulation between active area and bond pads allows for easy placement of the functionalization layers without shorting of leads to the bond pads. The bond pads allow easy connection to the outside world, i.e. easy packaging into chip carriers, DIP (Dual inline package), TO-type header, and other type packages convenient for use to hook into electronic circuits.

One embodiment of the present invention, a sensor platform 100, is illustrated in FIG. 1. In this embodiment, the sensor platform 100, shown in cross sectional view, comprises a substrate 110 including both a substrate Si wafer 110a with a surface sacrificial layer 110b with a first insulating surface layer 112 on top; a microstructure of first conductive layer 115 deposited in one or more patterns on the surface to make several devices, wherein the first conductive layer 115 comprises a first pair of sensing elements or filaments 120, wherein the filaments are disposed above and parallel to the semiconductor's substrate 110 with an air gap 121 between the base of the filaments and the surface of the substrate created by etching away part of the sacrificial layer 110b in the area under the sensing element which is a part of the conductive layer 115; a second insulation layer 117, wherein the second insulation layer 117 is configured such that the first pair of filaments 120 on the first conductive layer can remain exposed and are not covered by the insulation layer and/or a second set of sensing elements or filaments are covered and encapsulated by top 117 and bottom 112 insulating layers; and on top of the encapsulated (shown) or the unencapsulated filaments there can be none or one or more functionalization layers 125 deposited and touching the exposed pair of filaments 120 of the polysilicon layer that is exposed and not touching when the polysilicon is encapsulated by the second insulating layer. The functionalization layers 125 are adapted to provide one or more transducer platform classes selected from the group consisting of: radiant, electrochemical, electronic, mechanical, and thermal sensors. There is a separate passivation layer 126 that can be used to provide passivation of the leads from the active sensing element are of the chip to the bonding pads and cover any conduction leads on the chip to insure the robustness of the structure.

Figure 2A:
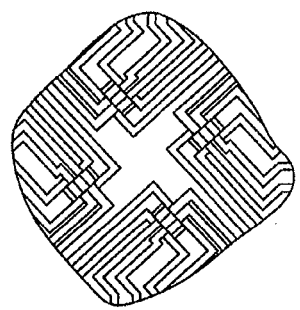
FIGS. 2A-D are top views of patterns of microelectromechanical sensor platforms according to exemplary embodiments of the present invention.
Figure 2B:
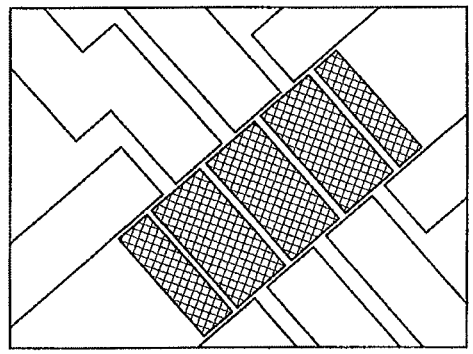
Figure 2C:
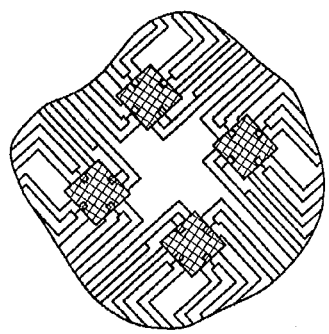
Figure 2D:
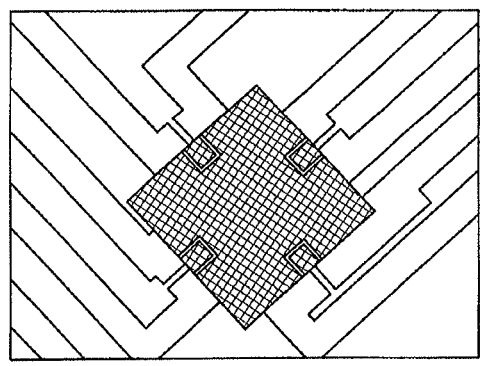

Another embodiment of the present invention is a method of manufacturing the sensor platforms. In this embodiment, the sensor platforms are fabricated by p-type silicon wafers upon which a sacrificial layer of more than two microns of silicon oxide is deposited. In one exemplary embodiment, loop bridges can be fabricated and suspended on the four edges of a square well (FIGS. 2C and 2D) and/or straight bridges (FIG. 2A, 2B, 3), bridging a long, narrow well can be fabricated. The polysilicon conductive portion 120 can be patterned to form loops or bridges of different sizes, such as 1, 5 or 10 microns wide, and 25, 50, or 100 microns long. The polysilicon can be made conductive to different levels by doping and the polysilicon can then be coated with an insulator 117 on top (there is already insulator on the bottom, 112) such as silicon nitride to make them passivated for TCD measurements and in this case the contact 127 and the functionalization layer 125 are not needed for only TCD measurements. The structures can also be coated with aluminum, platinum or Gold or other conductors to make conductive contacts, 127, and then devices can be made thereon with resistive measurements made between and across functional layers as illustrated by the R and C in FIG. 1. The passivation, 112, 117, 126, allows the polysilicon part of the device to be robust. The active element is the part that can be heated and made active for sensing, 120. Selectively etching the conductive and passivation layers creates devices that can be functionalized only in the required active areas for chemiresistor or chemicapacitor or transistor devices independent from the leads and bond pads or in the case of unfunctionalized and encapsulated devices that are thermistor or TCD thermal sensing elements. FIGS. 2A-D illustrates exemplary structures containing 4 bridges with 8 leads or 16 bridges for a total of 32 leads. FIG. 2A illustrates a photomicrograph of the center of a chip area of straight bridges that can be undercut so they are: 1] suspended, encapsulated, and unfunctionalized for TCD applications or 2] suspended, partly exposed and used with functionalizations, or 3] suspended, encapsulated, conductive deposits, 127, for electrodes and functionalized, 125, to create chemiresistors, chemicapacitors, or transistors [active semiconductor devices] on top of the polysilicon which can now function as a bottom gate for transistors or as a heater-temperature controller for sensing devices for example. FIG. 2B is a close-up illustration of straight bridges for one structure of the four areas on the same chip. As one skilled in the art will appreciate, redundant structures allow for easy evaluation, parameterization of response and processing, multiple devices on a single chip, and the estimation of yield and process issues during production. In addition, the cost difference between building one or twenty structures on the substrate in the MEMS world is an insignificant difference. FIGS. 2C and 2D illustrate photomicrographs of loop bridges according to another embodiment of the present invention.

In one exemplary embodiment, active sensing areas are made to contain 4 bridges so that they could be operated in pairs or sequentially for longer lifetime for the device. There are generally multiple areas on each die so that there could be multiple devices on each die.

In an alternative embodiment, the nano-sensor platform can be functionalized with nanostructures such as carbon nanotubes or CNTs and/or composite materials like CNT/polymer mixtures or many different materials to realize humidity and a large number of chemical and biochemical sensors. The functionalization of this MEMS structure with metal oxides can be used to create a versatile number of chemiresistor or chemicapacitor sensors for gases like ozone, CO, or hydrocarbons. In addition, the polysilicon can function as a bottom gate in a bottom gated FET if the polysilicon 120 is encapsulated. Further, because of the multiplicity so easily achieved in MEMS, many of the same kind or many different sensors can be prepared on the same substrate by applying the required functionalizations to different areas of the MEMS die that is populated with one or more of the versatile sensing platforms. It has been shown that heterogeneous electronic noses (containing many differently operating sensors and sensor principles) are more powerful that the homogenous ones, i.e. sensor platforms that can house more than one class of sensors simultaneously are more powerful than those with only a single type of sensor. And, in the description herein, we easily demonstrate electrochemical [amperometric], electronic [chemiresistor], and thermal [thermal conductivity] sensors on a single multifunctional die. In one exemplary embodiment, selective coatings for elevated temperature sensors are possible on the filament/bridge sensors, wherein the coatings are capable of operation at high temperatures with and without the conductor electrode over the insulation layers.

Other exemplary embodiments of the present invention include: The bridges configured with and without insulation and/or protection layers; the bridges configured with and without functionalization layers; on elements without passivation (conductive element exposed) functionalization layers with electrolytes can be used to make electrochemical sensors; functionalization layers with metals such as Pt to make combustible gas sensors; functionalization layers with metal oxides to make electronic sensors like chemiresistors and chemicapacitors and similarly functionalization layers with lower temperature polymers to make chemiresistors and chemicapacitors that function at room temperature; and functionalization layers with sorbents to make preconcentrators.

In one exemplary embodiment, the multiple areas on a single substrate are utilized to make arrays of the same or different devices including sensors, preconcentrators, transistors, or other devices used in fluid analysis and detection.

Figure 3:
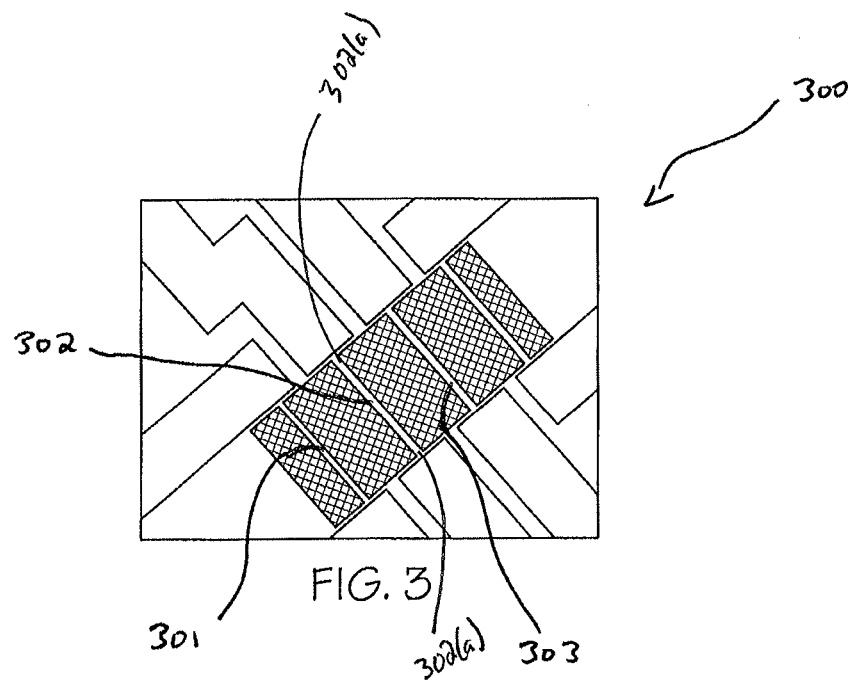
FIG. 3 is a top view of a pattern of a microelectromechanical sensor platform according to an exemplary embodiment of the present invention.
Figure 4A:
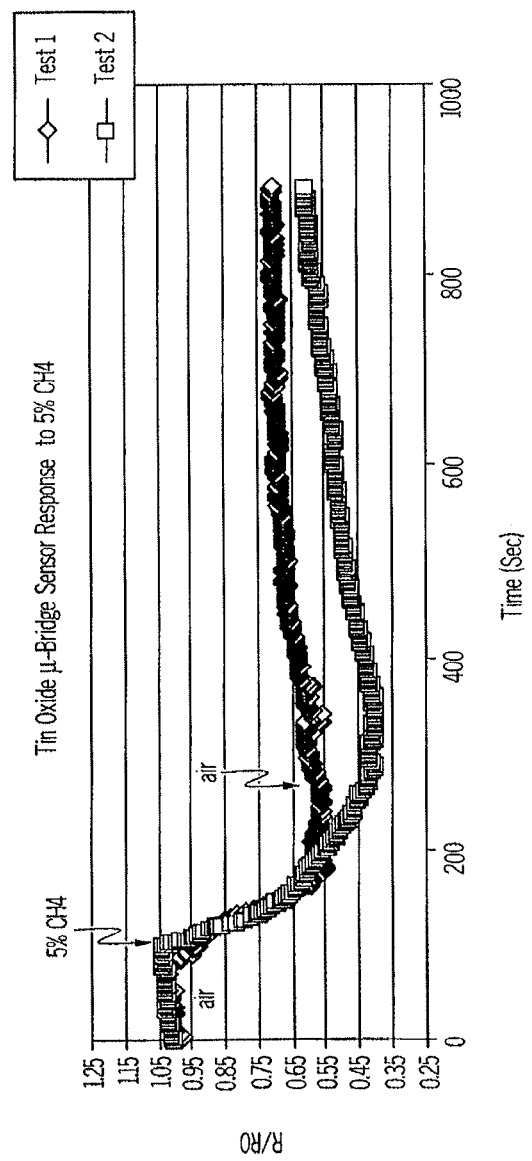
FIGS. 4A-B are sensor response charts relating to exemplary embodiments of the present invention.
Figure 4B:
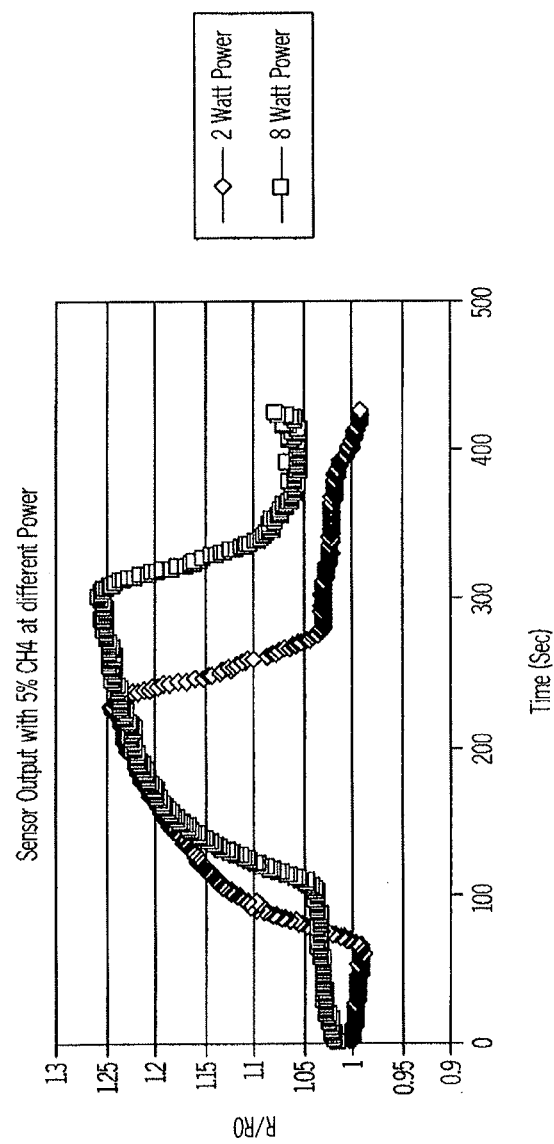

In another embodiment of the present invention illustrated in FIG. 3, a nano-sensor platform 300 is used to fabricate a combustible gas sensor. Bridge number two 302 is functionalized with tin oxide ($SnO_2$) layer. The sensor is then operated by passing current over bridges number one 301 and three 303 to heat the area and measuring the resistance of bridge two 302 (centered between one and three and obviously having means for reading the resistance of the $SnO_2$ layer, e.g., conductive electrodes leads 302a and 302b). In some cases the underlying bridge, 302, can be used as a heater and the SnO2 layer on top, with appropriate conductive leads can be used as the sensing resistor, as this is consistent with the Fig platform possibilities and descriptions. In this exemplary embodiment, the sensor is configured for testing with methane. FIGS. 4A-B illustrates the response of the sensor to 5% methane. As can be noted, the change in resistance is quite large and repeatable on two consecutive tests, but the recovery time may be slow compared to the response time and it is obvious that the devices have not yet been optimized for response to methane in these devices.

Figure 5:
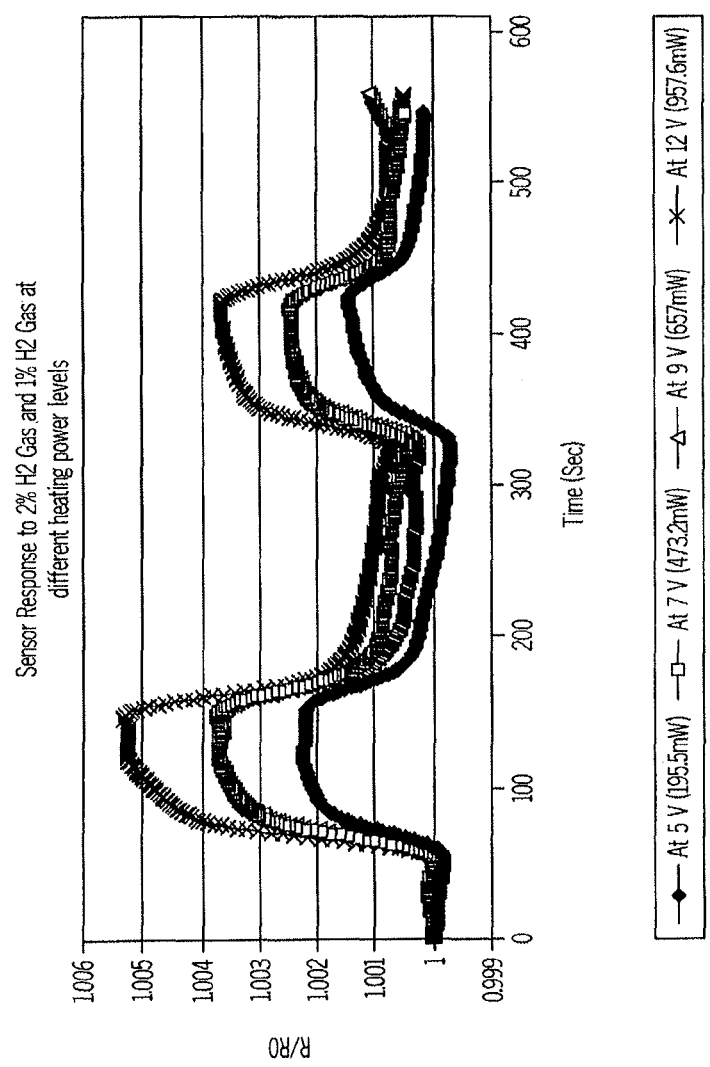
FIG. 5 is a sensor response chart relating to an exemplary embodiment of the present invention.
Figure 11:
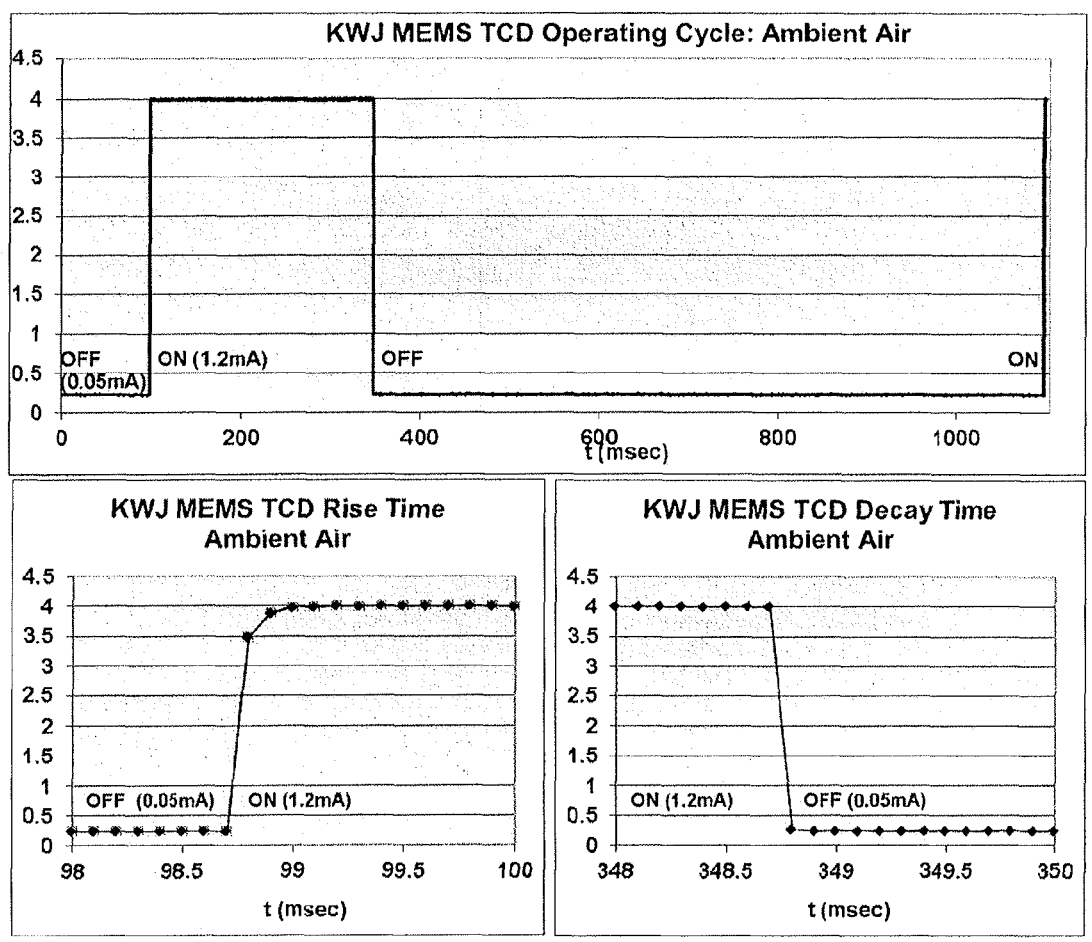
FIG. 11 illustrates sensor response charts relating to exemplary embodiments of the present invention.

In a similar embodiment, a second nano-sensor platform was unfunctionalized and encapsulated so it could act as a TCD element. This bridge was then used as the sensor, and heated to different power levels while exposing the sensor element to different gaseous environments containing hydrogen. FIG. 5 illustrates the response of the sensor to 2% and 1% hydrogen at increasing temperatures (applied power). As can be seen by one skilled in the art, this sensor showed a very rapid response and recovery to hydrogen and the response is most likely limited by the purging of the chamber and not the response time of the tiny MEMS element which we have found to be measured in nanoseconds. The power indicated in the graph legend is total power, across three filaments. One filament consumed approximately 100-200 mW. When the filaments are suspended and thermally isolated, we have found that they consume about 1 mA at 3 V or about 3 mW continuous duty but since they are so fast, they only need to be on for less than a microsecond to take a measurement. In such a case, the device can read once per second using less than 3 nano-watts or 1000 times per second using less than 10 microwatts. In the first experiments reported herein, the structures were not optimized for power consumption or response time, magnitude or selectivity. But rather these experiments demonstrated the feasibility of multi-classes sensors on a single platform. Later experiments have revealed that the sensors with a structure of 1×1×50 microns could detect hydrogen or other gas in air using only about 1 nanowatt of power per reading and with a response time of less than 100 nanoseconds to steady state signal. FIG. 11 illustrates results of these later experiments.

There are many adaptations of these above devices that will allow a variety of sensors and sensing capabilities to be realized. For example the lock and key electrode configuration is particularly suited for chemiresistors and chemicapacitors and electrochemical sensing. The bridges and filament elements are convenient for physical sensors like flow and thermal conductivity or temperature sensing but also can be used as electrodes (when not fully passivated and partially exposed) so that they also are amenable for electronic sensors [chemiresistors and chemicapacitors and active devices like chemically sensitive transistors] and electrochemical sensing. The elements that are filaments are the most versatile and thermal conductivity sensing for gases and binary mixtures is most common and so this new universal MEMS platform will be able to perform many gas analysis problems but with these new structures and implement different methods for analysis with greater versatility, lower power and MEMS advantages [e.g., size, cost] as can be practiced with the invention described herein. The many different fuctionalization layers that are compatible with the MEMS structures herein can create the many devices on a single platform that is truly surprising and novel. For example, functionalization with an electrolyte onto conductive filaments [not covered with insulator] or conductive patterns [lock and key] allow the realization of amperometric electrochemical sensors. Amperometric gas sensors [AGS] can be used for many analytes in gas and or liquid phases at room temperature and elevated temperatures [e.g. fluidic phases of matter]. Coating the same structure with polymers provides electronic sensors that can be used to detect many gases in air and is used frequently in electronic noses. Use as thermal conductivity filaments provides thermal sensors for binary and other gas mixtures. And all three very different sensing mechanisms (amperometry, electronic, thermal sensing) are all on the same platform when constructed as described herein. These sensors have heretofore required different platforms and herein we have a platform that can enable simultaneously electrochemical, thermal and electronic classes of sensors on a single substrate with appropriate functionalization or redundant structures.

Figure 6:
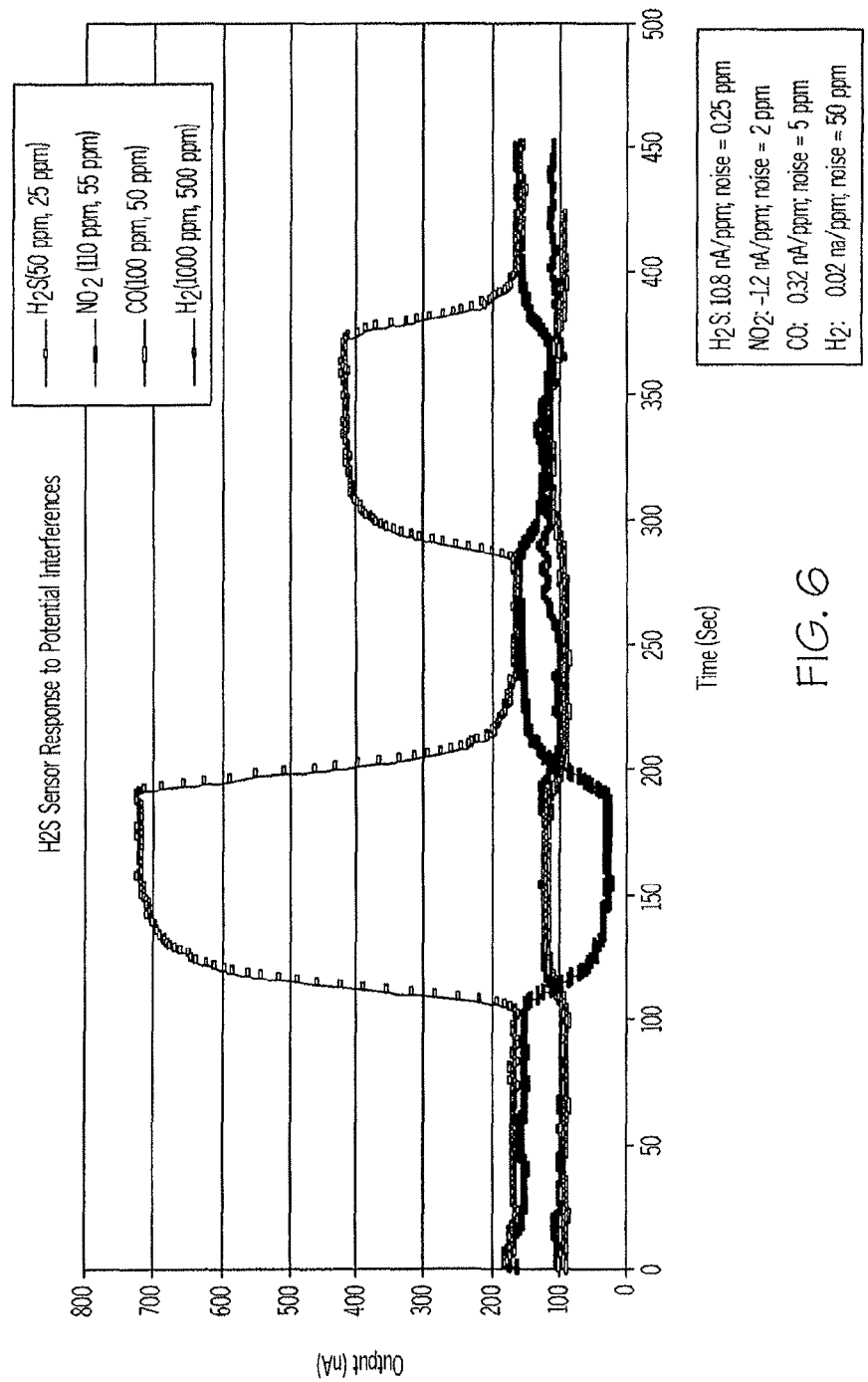
FIG. 6 is a sensor response chart relating to an exemplary embodiment of the present invention.

In one experiment, an electrochemical sensor is created on the platform. In order to create an electrochemical sensor, the bridge is functionalized with a platinum deposition using a proprietary form of the composite. The platinum particles of one micron or less in size (nano-particulate platinum) can be deposited by micro-pipetting onto four different regions of the bridge structure. In this case, the bridge elements serve as electrodes contacting the thin and discontinuous platinum particle film. A thin film of electrolyte (as the functionalization layer) is placed over the surface of the electrodes providing an electrolyte bridge between the platinum particle functionalized polysilicon electrodes. FIG. 6 illustrates the initial results for this functionalized electrochemical system when the sensor is challenged with samples of different electrochemically active gases. The sensor is optimized for $H_2S$ (sensing electrode bias=0 mW vs. Pt/air), and tested with four different gases—hydrogen sulfide, carbon monoxide, nitrogen dioxide, and hydrogen. The electrolyte used for these preliminary tests is a thin film of sulfuric acid, and no effort was made to isolate the referenced electrode. As shown in FIG. 6, the hydrogen sulfide response is quite stable and linear with concentration. Whereas the other three gases show responses of much lower magnitude. The carbon monoxide response on a per ppm basis is several thousand times smaller than the $H_2S$ response, providing excellent selectivity for this sensor. The CO response can be reduced even more with the use of a gold catalyst for the working electrode, and the $NO_2$ response can be minimized with an appropriate sensing electrode bias.

Figure 7:
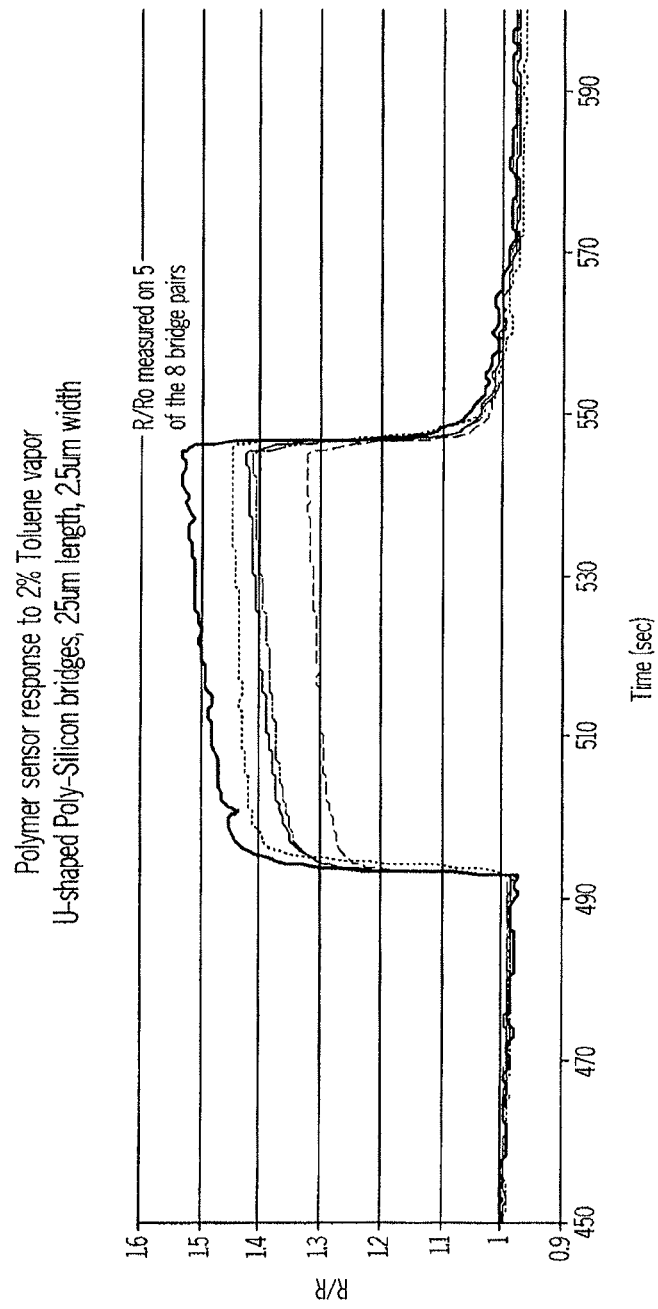
FIG. 7 is a sensor response chart relating to an exemplary embodiment of the present invention.

Yet another experiment on this same platform sensor was conducted to create a conductive polymer sensor on the sensor platforms of the present invention. To test a third sensor class on the same micro-bridge platform, a polymer bridge with nano-particulate carbon and with single walled carbon nano-tubes was coated on the MEMS sensor platform. This sensor will absorb vapor molecules, for example toluene, and exhibited a change in physical properties such as resistance or capacitance. In this experiment, the resistance of the film was monitored when the sensor is exposed to toluene vapors. The change in resistance as measured across five of the eight bridge pairs while the device was exposed to approximately one percent (or 10,000 PPM). The response from these five functionalized layers is shown in FIG. 7. Signals were obtained from three carbon materials: nano-particles, nano-structured carbon, and purchased single wall carbon nano-tubes that are 90% pure. All formulations produced responses as illustrated in FIG. 7.

As can be seen from the experiments above, the polysilicon bridges form the foundation for multiple classes of sensors. In the experiments above, three classes of sensors were demonstrated, thermal (catalytic and thermal conductivity), electronic (heated metal oxide or mox, and polymer or polymer composite chemiresistors), and electrochemical (amperometric sensor for $H_2S$ and other electro-active gases).

The present invention comprises a single platform having an electrode array on a dielectric material compatible with several sensor classes with various patterning of electrodes, passivation and encapsulation, and functionalization layers that enable different sensor classes and types to be built on the same platform with the distinction of being thermally isolater and low power and small in size. Thus, the same single platform can have multiple functionalization layers and different classes of sensors addressing different target analytes with different specifications. In one exemplary embodiment, the devices formed on the platform are configured such that they operate in an elevated temperature at very low power, such as less than ten mW and recently less that 1 mW continuous, or a few microwatts in intermittent operation.

Figure 8A:
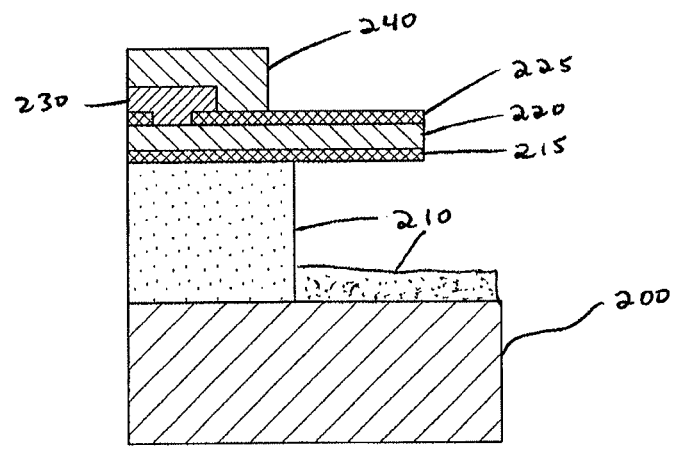
FIGS. 8A-B are cross-sectional illustrations of microelectromechanical sensor platforms according to exemplary embodiments of the present invention.
Figure 8B:
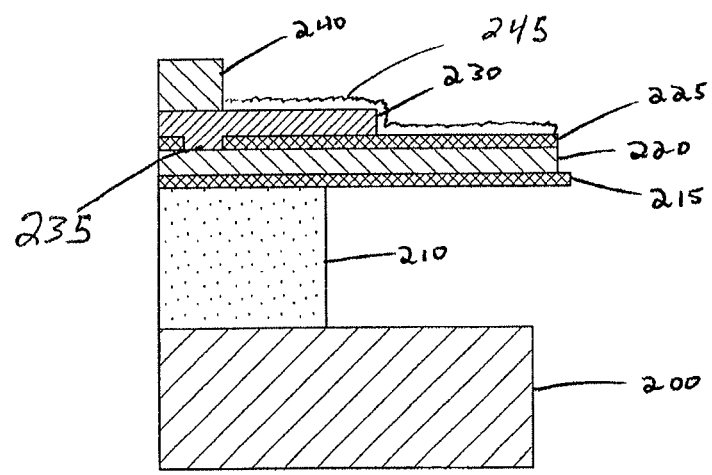

One embodiment of the present invention is illustrated in FIG. 8A. In this embodiment, a micro-bridge sensor chip platform cross section where the sensing element 220 meets the edge of the substrate 200 (to the left) and is extended over the open area to the right is illustrated. FIG. 8A illustrates a cross-section of a bridge platform according to one embodiment of the present invention. The platform of exemplary FIG. 8A is passivated or encapsulated by insulating layers 215 and 225. In this embodiment, the universal microelectromechanical nano-sensor platform comprises a semiconductor substrate including a surface, such as a silicon wafer 200, a microstructure sacrificial silicon dioxide layer 210 deposited in a pattern on the surface of the substrate silicon wafer 200. In the middle of the silicon nitride layers 215 and 225 is our patterned polysilicon layer of the sensing element layer that is patterned so as to make several devices wherein the polysilicon layer 220 is doped to the desired conductivity level to create the bridges as indicated by the structure comprised of 215 and 220 and 225 suspended over the substrate 200 wherefrom part or all of the sacrificial layer 210 has been selectively removed. The silicon nitride layer 215 is a passivation layer for the silicon oxide 210 and forms an encapsulation layer for the polysilicon layer 220 that can be deposited on top of 215. The polysilicon layer 220 is conductive, and can be used as resistive heaters, temperature measurement, and as electrodes (when part of the element is exposed to the functionalization layer). The platform further comprises another layer of silicon nitride 225 over the polysilicon, etched to have an opening to allow an aluminum layer 230 to be an electrical contact with the polysilicon layer 220 in the region that is not suspended. The Al electrode has contact with the poly through such holes from the sensing element to the bonding pad area of the chip and many metals can be used including Pt, Au, Pd or Al. In one exemplary embodiment, an encapsulation layer 240 is placed over the aluminum layer 230 to provide environmental and other protections to the layer. Of course, other layers are possible depending upon the maximum temperature of operation and the environment for the sensor that is expected. Another exemplary embodiment is illustrated in FIG. 8B, in which the platform electrode runner 230 is not completely passivated and the contact with the substrate through layer 235 is optional. In this case the conductive element 220 can act as a heater and or temperature sensors and the contact metal 230 can act as an electrode in contact with any suitable functionalization layer 245. Further, it may be important that the elements be constructed from layers of materials put down under tension so that stress does not cause early failure of heated devices. In fact, recent measurements have been made to show that this approach, heretofore unknown, is essential to long time trouble free operation of such a tiny device made from these thin layers. We further know that annealing of the layers is also important to final sensor performance.

In one exemplary embodiment, the sensor platform comprises one or more electrodes having polysilicon bridges and the electrodes are functionalized and have a width of one micrometer wherein the sensor platform has power consumption well below 50 mW. In recent measurements the 1×1×50 micron element has a power requirement of 1.2 mA at 3 volts or about 3.6 mW continuous operation but since the element operate with a response time of 100 nanoseconds or less, the device can take one reading per second for a power budget of less than a nanowatt per reading (thus powered at 1 nanowatt with one reading per second or 1 microwatt with 1 reading per millisecond and these rates are often perfectly acceptable for gas detection and monitoring). In another embodiment, the polysilicon sensing element [suspended and thermally isolated bridge structure] is functionalized with a catalyst, wherein the catalysts is configured such that the polysilicon bridge becomes a combustive gas sensor. This CGS can also be operated at very low power, much lower that any such device heretofore [the typical CGS uses about 1 W continuous power and has a slow response time].

Figure 9A:
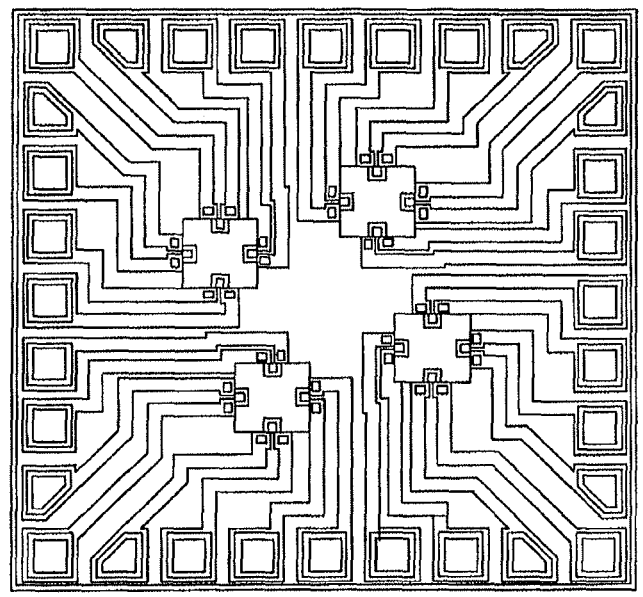
FIGS. 9A-B are top views of patterns of microelectromechanical sensor platforms according to exemplary embodiments of the present invention.
Figure 9B:
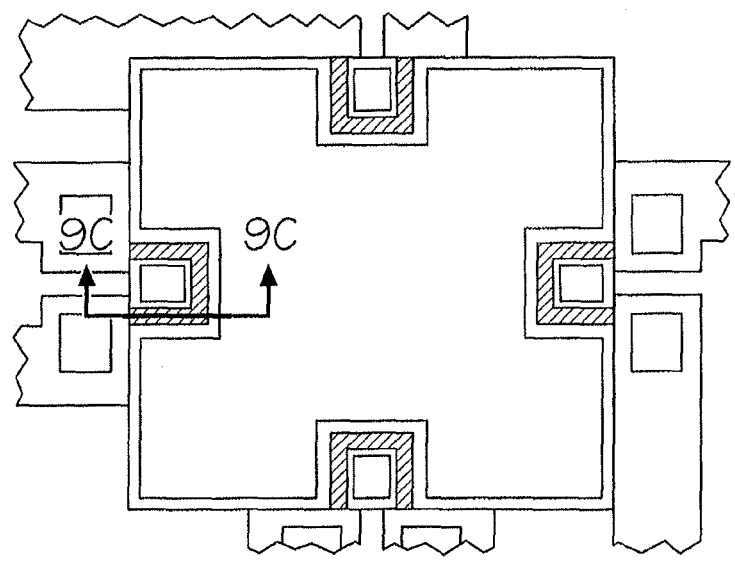
Figure 9C:
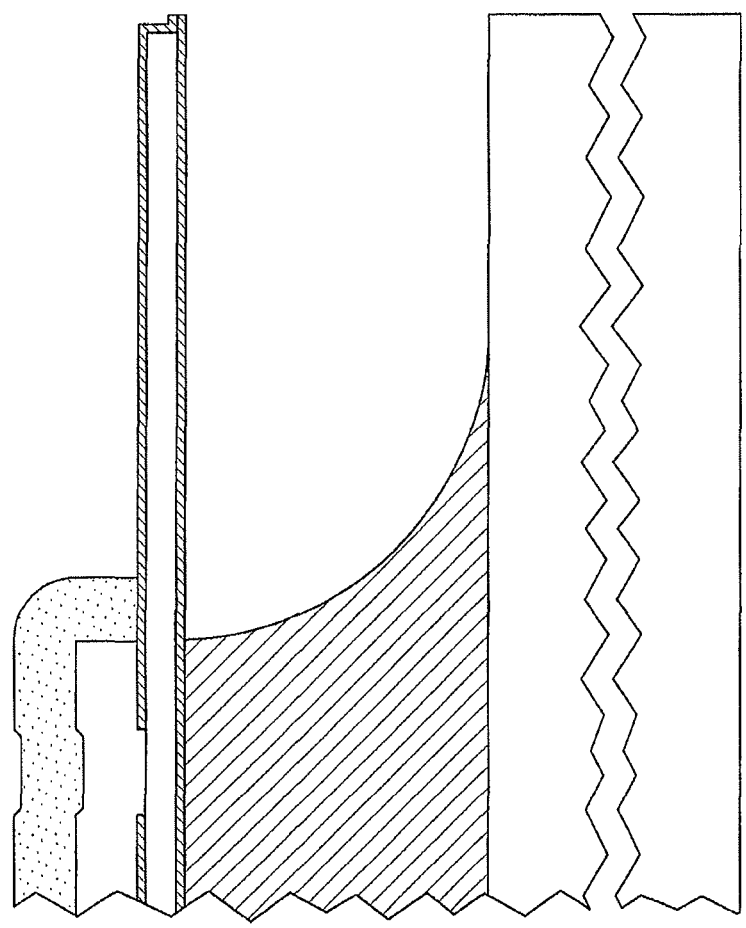
FIG. 9C is a cross-sectional illustration of a microelectromechanical sensor platform according to exemplary embodiment of the present invention.
Figure 9D:
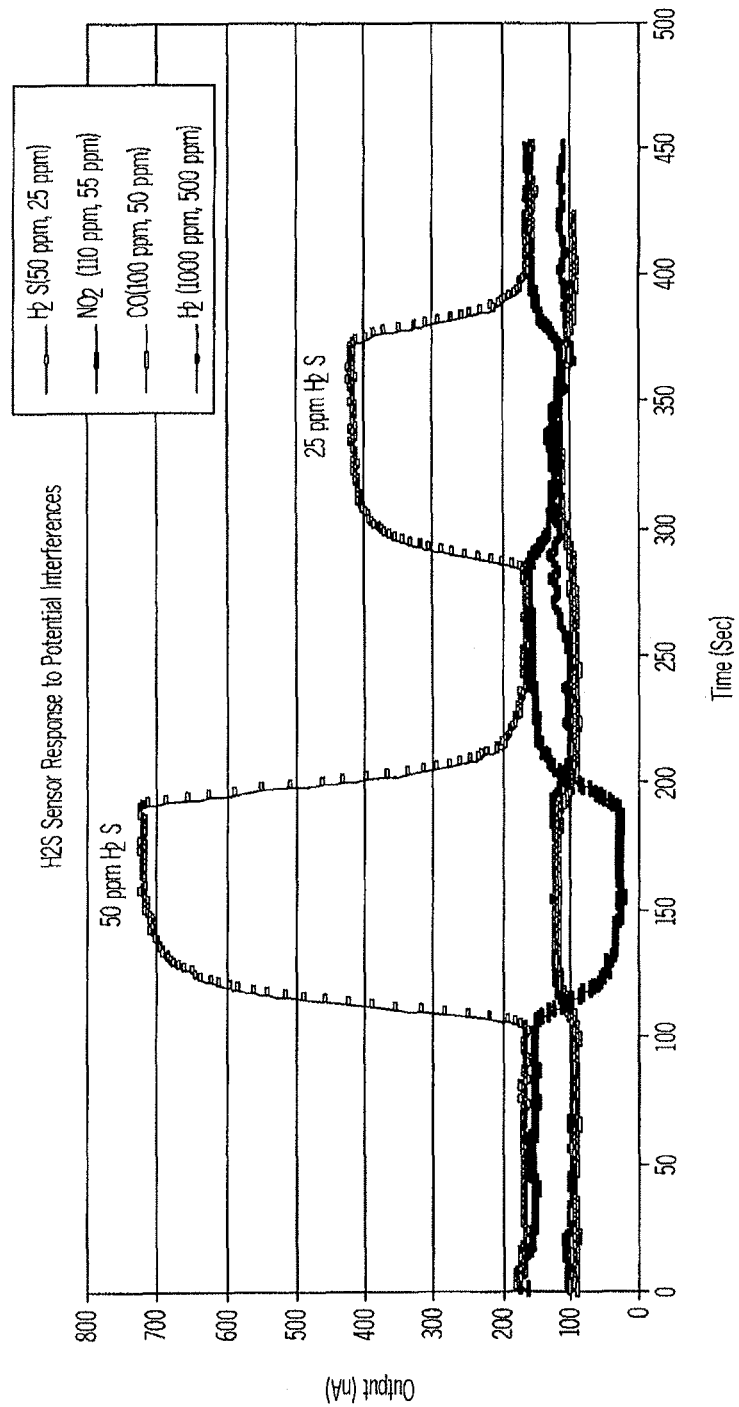
FIG. 9D is a sensor response chart relating to an exemplary embodiment of the present invention.

Illustrated in FIGS. 9A-C is another exemplary universal MEMS nano-sensor platform according to an embodiment of the present invention. In this embodiment, the sensor contains electrodes on a substrate. In one exemplary embodiment, the substrate contains a heater and a temperature sensor. The universal MEMS nano-sensor platform has a thermal sync configured for optimal/minimum power use at a given temperature. The platform comprises one or more sensing layers which are designed for multiple use, such as electrochemistry, electronic and thermal sensing. One or more functionalization layers are added to the sensing layers, and these functionalization layers add sensitivity, selectivity, and encapsulation from environmental insult. The MEMS chemical platform can detect virtually all the chemical analytes required in coal gasification: methane and hydrogen in thermal sensors, $H_2S$, carbon monoxide (CO), $NO_x$, $NH_3$, $Cl_2$, electrochemically, and hydrocarbons with electronic sensors.

Figure 10:
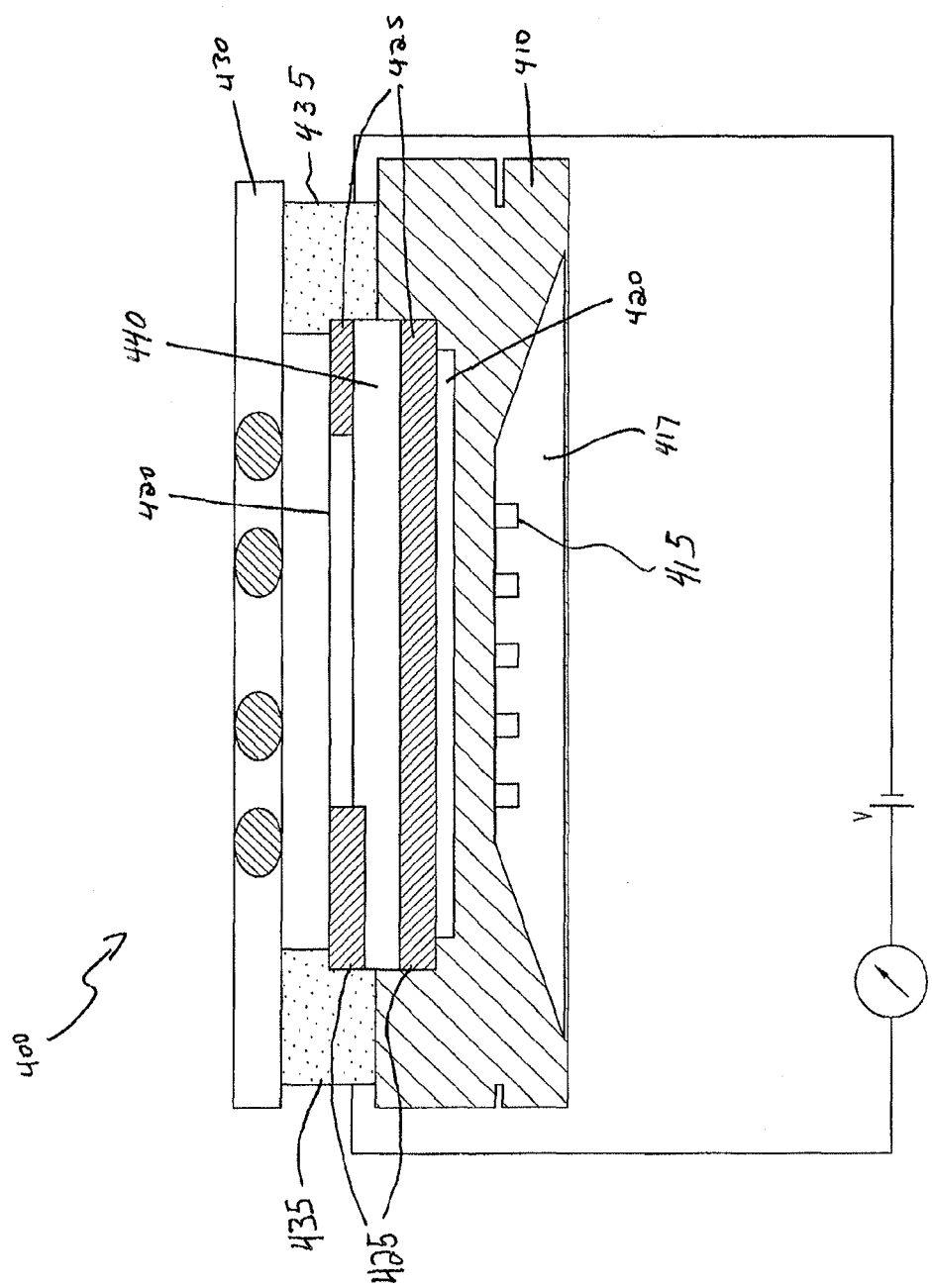
FIG. 10 is a cross-sectional illustration of a microelectromechanical sensor platform according to an exemplary embodiment of the present invention.

As illustrated in FIG. 10, the MEMS sensor platform 400 comprises a substrate 410 and one or more heater and temperature sensors 415 below the surface of the substrate 410 and located in the air gap 417 that is etched out of the substrate 410 in order to thermally isolate the sensing structure and reduce heater power consumption. In one exemplary embodiment, the heater and temperature sensor are embedded on the under side of the substrate 410, whereas in an alternative embodiment, a portion of the substrate on the opposite side of the surface in which a platform will be built is removed, and a heater and sensor is placed on the underside of the substrate 410. One or more sensing layers 420 can be deposited on the substrate sensing element 440. Or alternatively the layer 420 can be a passivating or encapsulating layer. In one exemplary embodiment, the sensing layers are deposited in a pattern comprising bridges and loops to create one or more sensing layers. On the sensing layer, one or more functionalization layers 420 are applied on the sensing element layer. The functionalization layers 420 may comprise one or more nanostructures which can add sensitivity, selectivity and encapsulation to the sensing layer. An overall encapsulation layer 430 may be applied depending on the type of sensor class being built.

In one exemplary embodiment of the present invention, the polysilicon layer is deposited in a pattern on the surface of the substrate in a lock and key electrode pattern. This lock and key pattern comprises an array and allow the electrodes to be used for capacitive and resistive measurements as well as a four-point probe as is illustrated also in FIG. 1. In one exemplary embodiment, the platform can have variable length polysilicon bridges. In this embodiment, the bridges can be used for heating and the sensing layer can be deposited onto an exposed aluminum lead forming a sensing layer as illustrated in FIG. 8B.

Unobtrusive, small, lightweight and energy efficient monitoring devices combining communication equipment and various sensors for detection of hazardous gasses, surrounding environmental conditions and personnel vital signs are possible through utilization of the above detailed MEMS technology. The diminutive size of the device is key to its effectiveness, as a first responder is far more likely to actually utilize a smaller, less obtrusive version of a device when compared to a larger, more interfering device. Another advantage is the energy efficiency of a monitoring device utilizing MEMS technology sensors. For example, a particular MEMS technology carbon monoxide sensor uses less than 10 µW of power. Even in embodiments utilizing a collection of MEMS technology sensors, the power usage for the device, including electronics for communication, amounts to less than 300 µW. Thus, a very small battery may be used to power the monitoring device, further contributing to its overall diminutive size, and thus, its effectiveness.

The present MEMS sensor platforms led to the following results and discoveries:
1. Selective detection of H2 was achieved with the Pd film hydrogen sensor, operating at 100° C. (<1 mW continuous operation, <10 µW at 1% duty cycle) since it responded to 0.25% $H_2$, but has no response to 100% He and >5% $CH_4$ in air. The exemplary micro-watt powered sensor platform for HMOx and $ZrO_2$ sensors with the $SnO_2$ coated polysilicon bridges were heated to a temperature of >400 C, with a peak "continuous" power of <10 mW. Responses to LEL (Lower Explosive Limit) levels of $CH_4$ were obtained. It is believed that pulsed operation with a 1% duty cycle (10 msec/sec) would reduce power consumption to <100 µW and optimization of the HMOx coating would yield ppb and ppm level responses.
2. The exemplary embodiments demonstrate three models and selective sensor element operation [e.g. at multiple currents] that offer discrimination between $H_2$ and He, with no response to >2.5% He (<5 µW with 1msec/sec duty cycle). This alternative selective TCD sensor has no reactive coating, so is not subject to the drift and "poisoning" of HMOx and Pd films and could last up to 5 years between calibrations.

Exemplary MEMS Sensor Designs

Six exemplary individual die were designed and constructed, each with one or more sensing structures. The exemplary sensors were designed so that a single process and mask set were used in the fabrication. The sensor elements consist of a 1 um thick doped polysilicon heater embedded in an LPCVD silicon nitride film for passivation. The metallization and electrical contact are Platinum to allow higher temperature operation. In addition, two and four contacts are provided to measure the properties of a heated thin film of Pd and ZnO deposited as a functional layer. The novel exemplary designs allow evaluation of sensor platform response parameters including: power, sensitivity, stability, selectivity, and response time. The 6 exemplary die incorporated variations of the nano-TCD platform specifically: type A] the nano-TCD multi-element chips, and type B] The nano-TCD multielement chips with an overlayer of electrodes of differing design. The former structures represent a unique TCD that can, for the first time, offer selectivity with a smart-sensor approach. The latter three die are this same platform functionalized with the proven NASA lick and stick chemistries [1, 2, 3, 4, 5] for gas detection.

Type A Die Designs—for Operation as a Nano-TCD.

Three sensor chips were designed with multiple copies of the sensor elements on them. FIG. 12 depicts an exemplary polysilicon TCD Bridge which was the bases for the following three exemplary die designs:

Die 1: 50 µm×1 µm×1 µm [l,w,h] passivated polysilicon TCD sensing elements with 4 active thermally isolated and 4 reference elements not thermally isolated per die/chip with 18 bond pads.

Die 2: same as die 1 except sensing elements are 100 µm×2 µm×1 µm with 50 µm×1 µm×1 µm center passivated polysilicon elements—4 active and 4 reference per chip.

Die 3: same design as die 1 except the sensing elements are 25 µm×0.5 µm×1 µm passivated polysilicon.

NOTE: Die 1-3 (FIG. 12) also include a polysilicon heater which may be used for optional temperature control of the die to improve performance in variable environments.

Type B. TCD Sensor Elements with External Electrodes:

FIG. 13 depicts the Type B exemplary design with a polysilicon TCD Bridge with Pt electrodes. Exemplary Dies 4, 5, and 6 include Pt electrodes that lie upon and extend out onto the passivated polysilicon sensing elements.

Die 4: Similar to die 1 except the structures have Pt electrodes for 2 point resistivity measurement on top of the 50 µm×1 µm×1 µm sensing elements—one electrode is continuous [a Pt RTD] and 3 Pt electrodes have a gap. The 4 reference elements per chip are also included.

Die 5: Similar to die 2 structures except there are Pt-electrodes for 2 Point resistivity measurement on top of the 100 µm×2 µm×1 µm with 50 µm×1 µm center suspended polysilicon sensing elements—3 have a gap and one is continuous [a Pt RTD] with 4 passivated reference elements per chip.

Die 6: This unique design places 2 Pt electrodes on each passivated thermally isolated sensing element so that we can make a 4 point resistivity measurement on the 100 µm×2 µm×1 µm with 50 µm×1 µm center polysilicon elements. There are 3 active and 3 reference elements per chip.

Exemplary Sensor Fabrication of the Present Embodiments

Exemplary sensor fabrication was demonstrated, using a multi-step multi-mask process as follows depicted in FIG. 15:

Start from a Si wafer with a 10 µm thick thermal SiO2 layer (1);
Grow 0.2 um thick LPCVD SiN (2)
Grow 1 um polySi (3)
Dope boron in two levels: high and low
EBL patterning microbridges:
Dry etch polySi (4)
Grow 0.2 um thick LPCVD SiN (5)
UV litho to open SiN windows for Cr adhesion and Pt contacts using Window MASK 1 (6)
Dry etch SiN
UV litho to pattern the Pt wiring MASK 2
Evaporate Pt/Cr (7)
UV litho to pattern the Au bond pads using Au Contact MASK 4
Evaporate Au/Cr
UV litho to open the BOE release windows using BOE Window MASK 3
Dry etch SiN (8)
Wet etch $SiO_2$ (9)
Post Processing:
Align shadow MASK 5 over the ¼ wafer for sputtering of Pd or Tin Oxide thin film on sensor elements in the appropriate areas (Dies 4, 5, 6 only, with ¼ of wafer with Pd, ¼ with metal Oxide (ZnO or $SnO_2$), and the rest uncoated).

Dice the wafer.

Wire-bond the dies (the devices ready for characterization and used as gas sensors).

Optical photos were taken of the structures on each die from Wafer 1 and shown in FIG. 16.

Figure 17:
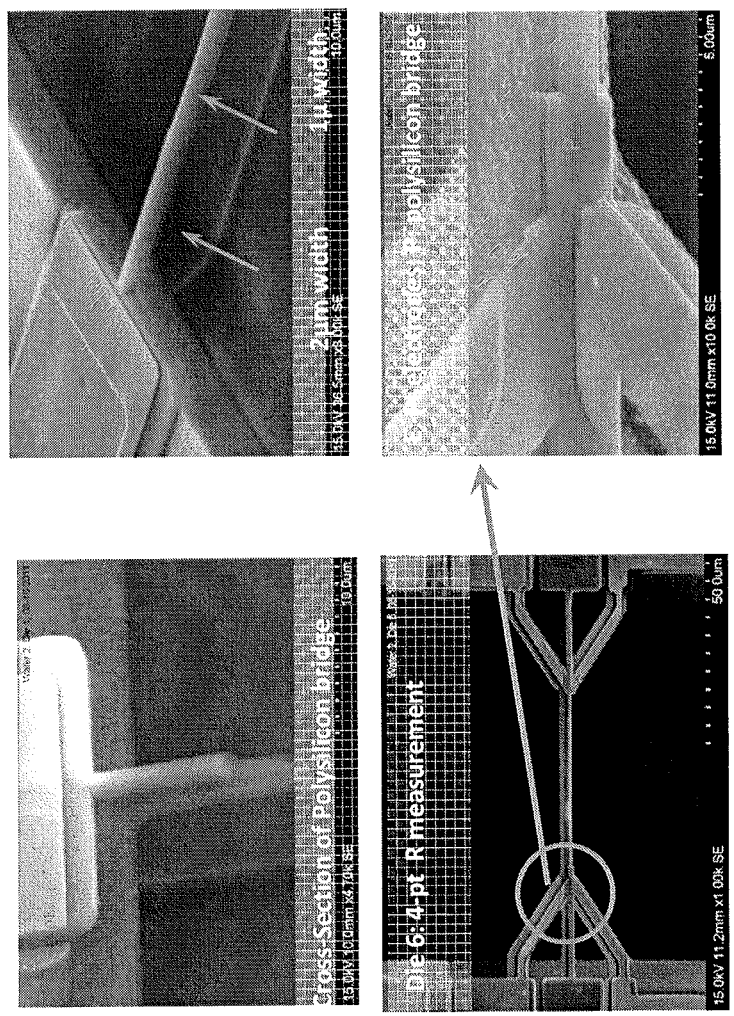
FIG. 17 illustrates images of exemplary embodiments of sensor platforms of the present invention.

Scanning electron micrographs were also taken to elucidate details of the structures illustrated in FIG. 17.

Exemplary Nano-TCD Sensor:

A circuit was designed and a PCB assembled from discreet electronic parts that will allow operating a MEMS sensing element at a programmable current, for a variable interval of time [FIG. 18]. This circuit is based on a Howland amplifier circuit and was built and debugged and then tested with a MEMS nano-TCD sensor of type A die 1 sensing element.

Commercial Benchmark KWJ TCD Sensor:

KWJ has designed and fabricated a TCD evaluation board [FIG. 18 right] for a commercial MEMS TCD element [Posifa Inc., San Jose, Calif.] and this board and TCD sensor served as a benchmark during the characterization of the innovative exemplary embodiment polysilicon nano-TCD element of the present application. The commercial sensor is operated by pulses of either 12 or 16 mA to the sensing element for a duration of 50-500 msec. This operation is controlled by the firmware programmed into the microprocessor on the board [an MSP430], and operation is fixed in hardware and firmware.

Both sensor boards produce an output suitable for input to a data acquisition routine such as PC with LabView. The commercial benchmark KWJ TCD with Posifa, sensor has an existing on-board calibration protocol, and a digital data signal that can be directly converted to % $H_2$. The new and innovative exemplary nano-TCD prototype circuit was programmed for Labview control of both data acquisition and signal processing. The data from these operational systems are compared and reported in the following section.

These circuits were used to collect data and develop and verify the models presented in the following sections. The sensor were placed in an environmental chamber for control of temperature and plumbed into a MFC-controlled dilution system to prepared gas mixtures of differing concentrations of H2, He and CH4 in air with and without various RH levels.

Exemplary TCD Sensor Results:

A selective TCD for $H_2$ or He and $H_2$ for a practical application [LEL detection in air using nano-watt power or leak detection in air with automatic T and RH correction]. The exemplary sensors also demonstrate feasibility of the nano-TCD platform to be used for functionalized sensors, i.e. coated sensors with active layers that can implement the NASA lick and stick selective detection [i.e., Pd for H2 and HMOx for LEL and low level HC detection].

The measured characteristics of the sensing elements are now presented:

Power Requirements:

The commercial Posifa MEMS TCD sensor element we used as a benchmark is believed to be the lowest power element currently available and when operated with the proprietary KWJ circuit and KWJ protocol, it used between 6 and 60 mW of power [approximately 15 mA at 4 V continuous and typically operated at 10% duty cycle in the KWJ protocol].

In contrast, the exemplary nano-TCD sensor of the present invention operates at a peak current of about 1 mA, at about 4 volts for a maximum power requirement of 4 mW and since the exemplary TCD can be pulsed 1000× faster, the ultimate power requirement is <50 uWatts. This will make the power consumption of the exemplary sensor comparable to the best discreet circuit elements [a first level achievement in chemical sensing] and enable the chemical sensors to be used with power harvesting and wireless circuits.

It is believed that the exemplary TCD sensors of the present invention are the first TCD [heated thermal sensor] to have a power requirement comparable to traditional ultra-low power electrochemical sensors and discreet electronic components. By variation of the width and amplitude of the power to the sensor element, the information content of the sensor output in increased such that we can achieve both ultra-low power operation as well as simultaneous quantitative and qualitative analysis of the gas mixture.

Response Time:

TCD: The Exemplary nanoTCD was operated using a 1.2 mA pulse [250 msec "ON", 750 msec "OFF"] and the sensor response [rise and decay] are illustrated in FIG. 19. The response time here is limited by the electronics and not the sensor element. But even in this case, we observe that the signal is at steady state in 100-300 micro-seconds. The implications of this simple test are that the duty cycle can be less than 1 msec and therefore the power of this element is estimated to be 4 mW, with 1000 readings per second or 4 microwatts with one reading per second. This provides us with many options for tuning the power requirements to the application for distributed sensing or portable instruments or in-flight use.

Sensitivity and Linearity:

To obtain a signal for $H_2$ in air, the signal from the sensor must be recorded for both air and $H_2$/air mixtures. The analytical signal is the difference between the signal for air and the signal for $H_2$/air. An example is illustrated in FIG. 20 where we record the sensor resistance at constant current in different gas mixtures. When the sensor signal is plotted as the gas environment is changed, we obtain the results shown in FIG. 20. The signal to noise for both commercial sensor and the exemplary KWJ nano-TCD with the KWJ circuits and protocols are excellent when operated in the pulse mode. Note the slight baseline drift in both sensors, corresponding to approximately 900 ppm $H_2$ for both sensors. This drift in uncompensated signal is due to a temperature change during the test [see lower panel in FIG. 20].

We conclude from this test that the exemplary operating protocol is an excellent way to measure concentration of $H_2$ in air with the TCD. Furthermore, this data demonstrates what has heretofore been the "Achilles heel" of the TCD sensor, the need for extremely precise temperature control and compensation through an algorithm or precisely matched reference elements. However, the exemplary pulsed mode operation and compensation algorithms of the present invention allows us to compensate for temperature with only a single TCD element.

Exemplary Computational Approach for Sensor Calibration and Data Analysis.

The TCR [temperature coefficient of resistance] has been measured for the nano-TCD [Die 5 thermally isolated structure, suitable for decoration with a sensing layer]. Resistance data is collected in an oven, by recording resistance vs. T over the range 20° C. to 200° C. and is illustrated in the FIG. 21.

The TCR for these elements is stable and the data from both the nanoTCD and Benchmark TCD are stable over long periods of time. And these data support the conclusion that our target of 5 year lifetimes without calibration is feasible with these MEMS structures. We did not see any drift over the entire 6 months of testing and the benchmark MEMS sensor has been stable for more than 1.5 years. The nano-TCD with multiple elements per chip could lead to extended lifetimes for the chip in excess of 20 years using the current exemplary designs.

Exemplary Compensation of MEMS Thermal Conductivity Sensors for Temperature-Independent Hydrogen Measurements.

Overview:

The response of the TCD is measured with exposure to a constant concentration of hydrogen. The sensors are pulsed "ON" long enough to allow the temperature to stabilize, then turned off until the sensor returns to ambient temperature. Specific protocols for the two sensors are as follows:

The Benchmark MEMS sensor [Posifa Inc, San Jose, Calif.]. The KWJ protocol pulses the current on the active sensor, and reads points on the decay curve as it cools back to ambient. The KWJ operating protocol for the MEMS element is:

Pulse current for 100 mSec ['ON']

Reduce current to 1 mA [no heating occurs] and read resistance for 20 mSec as the sensor cools, [current is 1 mA while reading resistance]

400 mSec 'OFF' [also at 1 mA]

Although the exemplary nanoTCD is much faster responding than the commercial sensor, for consistency of data we operated at approximately the same duty cycle for this study:

Pulse the current to 1.2 mA for 250 msec 'ON'.

Reduce current to 50 μA for 750 msec 'OFF'.

This cycle is repeated continuously. The resultant data is ported to a PC via a Labview data acquisition program and processed:

For the KWJ benchmark sensor, the data provides a decay curve over 20 msec. The element temperature returns to ambient room temperature within 20 mSec. The data point at 400 μSec is taken as $R_{max}$ as it was observed to be the most precise point on the decay curve [the smallest standard deviation was observed at this point]. In each case, the A/D counts are recorded and are converted to voltage. We calculate the resistance from the measured voltage and known current and plot the sensor element decay curve as resistance vs. time. The sensor was operated at 16 mA and 12 mA [FIGS. 22a and 22b].

Exemplary Detailed Sensor Calibration Procedure:

Definition of Variables:

$R_{max}$: resistance of sensor 0.4 mSec after turning off current—the "hot" resistance. The 0.4 mSec point has the best precision for the hot temperature. There are some electronic transients during the first few hundred microseconds.

$R_{min}$ resistance of the sensor 20 ms after turning off current—the "cold" resistance. Within 20 msec, the sensor has returned to "cold", or ambient temperature.

$dR=R_{max}-R_{min}$. This difference signal is related to the thermal conductivity.

$R_{avg}=(R_{max} R_{min})/2$. The average resistance, which is representative of the temperature at which we are taking the data—this is $T_{mix}$.

$R_{avg}/dR$—the average resistance divided by delta resistance is a dimensionless reduced or normalized resistance and is highly correlated to the thermal conductivity of the sample. We call this variable λ, and this is our "signal" for the benchmark TCD.

C1 and B1: slope and intercept, respectively, of regression of $R_{avg}/dR$ vs. $R_{avg}$ ($T_{mix}$). These factors are calculated for several % $H_2$.

C' and B': slope and intercept, respectively, of regression of C1 vs. % $H_2$. These parameters are calculated at different $R_{avg}$ ($T_{mix}$).

C" and B": slope and intercept, respectively, of C' vs. $R_{avg}$ ($T_{mix}$). These parameters are independent of $H_2$ concentration.

Calibration of sensors is performed in 2 steps:

i. Temperature Correction using self-compensation algorithm.

ii. Humidity Correction.

Step 1: Temperature Correction:

First the sensor response to hydrogen mixtures at different temperatures is measured to obtain the effect of temperature on hydrogen signal.

a. This experiment is performed by purging the test chamber with mixtures of Hydrogen in dry air to eliminate any interference from moisture b. Once the composition is stable, the temperature is slowly ramped up from 10 Deg C. to 30 Deg C. [any range can be chosen as this sensor is totally solid state and can operate sub-zero to several hundred degrees Celsius].

c. $R_{avg}/dR$ is plotted as a function of T ($R_{avg}$) for air and the different $H_2$ concentrations.

Typical experiments with this protocol are shown in FIG. 22. When the experiments are competed over the required T and compositional range, we have a data set. This data set can be collected for different $H_2$, He, or water concentrations, or any variable of interest. We can derive a set of equations to represent the data—a linear representation follows:

$$R_{ave}/dR = C1 * R_{ave} + B1 \qquad 3)$$

Note 1:

the above Equation (2) assumes a linear relationship over the temperature range. For the KWJ benchmark sensor, this turns out to be a very good assumption, and the following discussion utilizes linear equations for simplicity.

Note 2:

TC is a function of the gas pressure [e.g. see thermocouple and pirani pressure gages] and we assume the pressure is the same for all the above readings but there is also a pressure-dependence. We used a commercial MEMS pressure sensor to log the ambient pressure during measurements but the linear pressure compensation was not included in the analysis that follows. All tests are performed at sea level under nearly constant pressure.

For the novel exemplary nanoTCD, the data is not always fit by linear relationship. We get a very good representation of the value for R/dR at different temperatures using a polynomial, and this creates a slightly more complex but more data rich model [i.e. higher information content].

Real-Time Operating Algorithm for Measuring Temperature-Independent % $H_2$

In this exemplary procedure for sensitive, selective % $H_2$ in air analysis, we use the equation below, which is a variation of Equation (2):

$$[R_{avg}/dR]_{unk} - [R_{avg}/dR]_{0\%H2} = C'[\% H_2] \times 100 \qquad (3)$$

Substituting the known C' we obtain:

$$[R_{avg}/dR]_{unk} - [R_{avg}/dR]_{0\%H2} = C''_{Ravg}R_{avg} + B''] \times 100$$

Rearranging to solve for % $H_2$:

$$\%H_2 = ([R_{avg}/dR]_{unk} - [R_{avg}/dR]_{0\%H2})/100 * [C''_{Ravg}R_{avg} + B'']) \qquad (4)$$

Equation (4) is used to calculate the % Hydrogen in an unknown mixture at any temperature from a single sensor reading. The required calibration constants for the sensors, as defined above, are given in the Table 1 below:

TABLE 1

|  | 16 mA | 12 mA |
|---|---|---|
| Slope (C1)0% H2 | 0.051622 | 0.050241 |
| Intercept (B1)0% H2 | −5.646715 | −2.693357 |
| Slope(C″) | 0.069947 | 0.126951 |
| Intercept(B″) | −3.444073 | −5.263125 |

The sensor is now calibrated and temperature compensated and can be used for measurement of % $H_2$ in dry Air at any temperature. The procedure is as follows:
  Measure $R_{max}$ and $R_{min}$, for the unknown mixture at any temperature.
  Calculate $[R_{avg}/dR]_{unk}$ and $R_{avg}$.
  Using above equations and calibration constants, calculate for 0% $H_2$ the $[R_{avg}/dR]_{0\% H2}$ at the measured $R_{avg}$ and this provides the signal at 0% $H_2$ and Rave values for equation 4.
  Using Equation 4, and values for C″ and B″ for the appropriate sensor (12 or 16 mA), solve for % $[H_2]$. This is accomplished in real time by the Lanview data-acq program and also by the on-board uP.
  NOTE: the precision and the accuracy of this measurement depends upon the system [i.e., the sensor, the electronics, the method of measurement, the model algorithm, and software]. While the exemplary embodiment is not yet optimized, the method and the model have definitely demonstrated the feasibility of the approach to yield a compensated % $H_2$ measurement with sufficient sensitivity and accuracy for an % LEL alarm.

Exemplary Humidity Correction:

The second major environmental interference is humidity (RH), or more specifically the moisture content of the air. A Sensirion SHT15 RH sensor was installed on the sensor board to measure RH. The RH value was converted to ppm $H_2O$. Data for moisture compensation was collected as follows:
  1. The chamber is purged with a dry air (500 ppm $H_2O$).
  2. The measured $H_2$ was recorded at four concentrations between 0 and 2.5% $H_2$.
  3. Measurements were made at 3 additional moisture levels—0.2%, 0.9%, and 1.2% $H_2O$.

From these room temperature data, it was observed that the RH effect on the measured % $H_2$ is a simple offset, proportional to the % $H_2O$. There is no RH effect on the slope (sensitivity). To confirm whether this simple relationship held over a range of temperatures, an additional test was performed:
  1. The chamber was purged with dry air (500 ppm $H_2O$).
  2. The temperature was increased from 10 to 30 Deg C., and the signal in air recorded as a function of temperature.
  3. These measurements were repeated with pure air at 4 additional moisture levels (0.4%, 0.57%, 1.00% and 1.35% H2O.

The resulting data is summarized in FIG. 23 and the following table 2 of signal vs moisture levels for Sensor 1 [16 mA] and Sensor 2 [12 mA], corresponding to two different operating temperatures.

TABLE 2

| 16 mA Sensor: | | | | | |
|---|---|---|---|---|---|
| % H2O | 0.05% | 0.400% | 0.580% | 1.000% | 1.35% |
| OFFSET | −0.00000003 | −0.0011 | −0.0015 | −0.0032 | −0.005 |
| 12 mA Sensor: | | | | | |
| % H2O | 0.05% | 0.400% | 0.600% | 1.000% | 1.32% |
| OFFSET | 9.51107E−06 | −0.0007 | −0.001 | −0.0015 | −0.0017 |

Once the temperature compensated value for % $H_2$ is obtained from Equation 4, we can correct for moisture (CF=correction factor) using the equations below:

$$CF(H2O)_{16\,mA} = -11.9441[\% H_2O]^2 - 0.2121[\% H_2O] + 0.0001$$

$$CF(H2O)_{12\,mA} = 7.1273[\% H_2O]^2 - 0.2326[\% H_2O] + 0.0001$$

The Final Equation for Temperature and Humidity compensated % H2 is given by:

$$\%H_2 = ([R_{avg}/dR]_{unk} - [R_{avg}/dR]_{0\%H2})/(100*[C''_{Ravg} \times R_{avg} + B'']) - CF(H2O) \quad (5)$$

Conclusion: We have demonstrated with a sensor array, a temperature and humidity compensated TCD. FIG. 24 illustrates a real-time output stable during temperature and humidity shifts.

The screenshot in FIG. 24 above illustrates the stability of the compensated signal in 2.5% H2, when the RH is reduced from 40% to 20%, and the T is increased from 20 C to 25 C.

Exemplary Nano-TCD Sensor Element

The response time of the exemplary nano-TCD is typically too fast for a simple electronic circuit to measure. In order to evaluate the nano-TCD sensor, we designed a constant current circuit to pulse from "cold" to a programmable "ON" or "hot" current. The prototype circuit also has an on-board T and RH sensor; as a reference for our "cold" measurement. The counts recorded are converted to voltage for the purpose of this model.

Initial tests were performed with the sensor on a short cable, suspended in the test chamber. The sensor was powered using a constant 1.17 mA circuit and the data recorded using a LabView protocol. In this case, we did not convert the TCD reading to resistance or temperature but rather used the voltage readings at constant current directly as analytical signals. We noticed very large temperature effects on the ambient current (in air) as well as in the "span" delta signal between air and $H_2$. This was corrected later wherein we demonstrated a very small T variation when the sensor was mounted directly to the new exemplary current controllable circuit designs. This new circuit illustrated the possibility for improvements in sensitivity and stability by optimizing the electronics. When the circuitry was laid out on a revised board, which accommodates the sensor plugging directly into the board, temperature effects are reduced by more than 10-fold.

Exemplary Smart Sensor

The exemplary smart sensor consists of two parts: 1] the sensor hardware and operating protocol that can generate the signal/data [$V_{max}$, in this case] from the sensors under several power levels, different operating conditions and 2] the smart interpretive model/algorithm that can extract the composition of the analyte gases and automatically compensate for humidity and temperature effects. In the above discussion we described the sensor and how it is made, the electronics and their design and calibration of the system. Here we describe the novel approach to operating the sensors and interpretation of the data to get advanced analytical performance.

First, the exemplary nano-TCD is a heated element, but the sensing element is so small it takes only nano-wattHrs to heat it to operating temperature for less than a microsecond. When we heat it with a constant current, the resistance changes [with the temperature] and the ultimate temperature achieved is a function of the rate of heat loss from the sensing element, i.e., we try to optimize the heat loss through thermal conduction of heat away from the element by the gas. Under these conditions, the final temperature is measured as the element resistance—or proportional to the final voltage [at constant current as used in the following models].

The exemplary smart sensor comprises of the thermal element, the operating protocol, model, and interpretive algorithm that allow both quantitative and qualitative analysis of the gas.

Exemplary Algorithms and Models for the Nano-TCD Sensor Embodiments:

This section describes novel models for temperature and humidity compensation with the TCD sensor so that is can be used in the presence of widely varying ambient conditions and for gas mixture analysis.

Model A: The simplest case involves operation under conditions with no relative humidity (RH) dependence or temperature (T) dependence. Model A is useful for the Pd sensor or HMOx sensor since these will be operated at constant temperature or for simple binary mixture analysis with a TCD.

Model B describes an algorithm to determine the hydrogen concentration using T and RH compensation using an embedded RH sensor and can be useful when the TCD is used with the sensor array.

Model C describes a method to estimate the temperature compensated hydrogen concentration without the use of an RH sensor (i.e., self-compensation). It is believed that Model C can be further developed and optimized so that the TCD can be used to automatically under any conditions for selective analysis of gas mixtures of three or more components.

Model A (No Relative Humidity or Temperature Dependence):

This model describes the typical application of a TCD for binary gas mixtures. The TCD can be used with $H_2$ in air [air is considered a single gas and invariant]. The generic equation describing the thermal conductivity of a binary gas mixture is given by the following equation [10,12].

$$\lambda_{min} = \lambda_1 \cdot \left(1 + G_{12} \cdot \frac{X_2}{1+X_2}\right)^{-1} + \lambda_2 \cdot \left(1 + G_{21} \cdot \frac{X_1}{1+X_1}\right)^{-1} \quad (6)$$

This can be simplified to a linear expression as follows:

$$TCD\ signal = m[H_2] + I \quad (7)$$

where m and I are constants [this was used in the above example TCD calibration of the benchmark TCD, herein is the theoretical justification].

This approximation is generally valid for most binary mixtures like 0-5% $H_2$ in air. However, the measurement is both pressure and temperature sensitive and one can typically compensate with an on board temperature sensor. Herein, we use the TCD signal itself.

The advanced exemplary sensor is operated in a pulsed mode. This allows much lower power requirements but also has the added benefit of enabling an ambient temperature measurement. Thus, from one cycle we obtain the temperature and the thermal conductivity and so we are able to automatically compensate for temperature per above discussion]. The above calibration discussion illustrated our Model A and the following equations and data illustrate the temperature compensated reading from the exemplary nano-TCD sensor and a more advanced model and compensation. Pressure correction may be important in some situations. In Model A, we will be able to operate the Pd or HMOx sensors at constant temperature in ambient conditions and obtain both the Pd and/or HMOx signal as well as the thermal conductivity to allow smart sensor operation!

Model B (External RH Compensation, Internal T Compensation):

In addition to temperature correction, the moisture [as % water vapor] in the gas mixture can change the thermal conductivity and therefore cause error especially in ambient readings of gas concentration with a typical TCD. In this case we improve our model and use surfaces to represent the calibration data over the ternary (hydrogen, water vapor and air) mixture thermal conductivity changes at different RH and temperature. This model describes the best fit of the nano-TCD data (sensor operated at 1.2 mA) to planar surfaces in 3 dimensions. FIG. 25 shows the data matrix with the voltage measured across the sensor during the passage of 1.2 mA ($V_{max}$) plotted as a function of T and RH. Each surface represents a particular concentration of hydrogen over a range of temperature and humidity. FIG. 26 shows the same data surfaces from another angle for clarity, and it indicates that they do not intersect and can therefore be approximated by parallel planes. It also implies that for a particular value of temperature and relative humidity, a value of $V_{max}$ correlates to a unique hydrogen concentration.

A plane in space can be represented as $Ax+By+Cz=D$, where x, y and z represent the coordinate axes. In our analysis the x-axis represents temperature, the y-axis represents relative humidity (% RH), and the z-axis represents the voltage measured ($V_{max}$) across the sensor at 1.2 mA. The equation representing the planes matching the data surfaces, becomes $$A \cdot T + B \cdot w + C V = D \quad (8)$$

where T≡temperature, w≡% RH, and V≡Vmax.

Parallel planes can be represented as $$A \cdot T + B \cdot w + CV = D_1,$$
$$A \cdot T + B \cdot w + CV = D_2,$$
$$\vdots$$
$$A \cdot T + B \cdot w + CV = D_n,$$

where each $D_i$ value represents a particular hydrogen concentration. The coefficients A, B, and C for the best fit to a single data surface can be used for all surfaces and the values obtained are:

$$\begin{pmatrix} A \\ B \\ C \end{pmatrix} = \begin{pmatrix} -7487 \times 10^{-8} \\ 5.621 \times 10^{-10} \\ 1.36 \times 10^{-5} \end{pmatrix}$$

The solution for D is a linear function of the hydrogen concentration, as can be seen from FIG. 26, and can be written as $$D = d_o + d_1 \cdot h,$$

where h is the [%] hydrogen concentration. The values of $d_0$ and $d_1$ are:

$$\begin{pmatrix} d_0 \\ d_1 \end{pmatrix} = \begin{pmatrix} 3.155 \times 10^{-5} \\ -3.01 \times 10^{-7} \end{pmatrix},$$

This leads to the following equation:

$$h = \frac{A \cdot T + B \cdot w + C \cdot V - d_0}{d_1} \quad (9)$$

The temperature and voltage are measured quantities, and using an embedded RH sensor to obtain relative humidity establishes values for all terms on the right hand side of the equation (9). The hydrogen concentration can then be calculated. Table 3 below shows the measured and calculated values of the hydrogen concentration using equation (9).

TABLE 3

Comparison of actual and calculated hydrogen concentration using Model B

| T (K) | % RH | [H$_2$] actual = 0.0% | [H$_2$] actual = 0.5% | [H$_2$] actual = 1.0% | [H$_2$] actual = 1.25% | [H$_2$] actual = 2.0% | [H$_2$] actual = 2.5% |
|---|---|---|---|---|---|---|---|
|  |  |  |  | Error in [% H$_2$] calculated |  |  |  |
| 294.702 | 2.647 | 0.041 | +0.125 | +.144 | +.147 | +.131 | +.024 |
| 303.873 | 1.108 | −0.133 | −.094 | −.008 | −.074 | −.097 | −.176 |
| 303.453 | 23.023 | 0.138 | +.195 | +.206 | +.221 | +.20 | +.108 |
| 295.102 | 34.593 | −0.112 | +.004 | +.03 | +.022 | +.003 | −.018 |
| 301.89 | 22.586 | −0.02 | +.032 | +.054 | +.056 | +.065 | −.004 |

This simple sensor and model is capable of determination of H$_2$ concentration in air with both variable RH and variable temperature with a non-drifting physical sensor that is stable for >5 years and works on nanowatts of power.

This yields a novel innovative exemplary Mems sensor with selective detection of H$_2$ or He in air [no interference from T, RH changes]. It is of course easy to see the extension of this model to compensate for any interfering gas [He, CH$_4$, solvents, etc.] as long as they are included in the initial calibration matrix!

While the signal has not yet been optimized over the range of temperature and humidity, and over different power levels, our data supports the conclusion that we can ultimately simultaneously improve the selectivity and the limit of detection for this sensing element as well as improve the accuracy/precision with an optimized operating protocol and optimized electronics to provide additional data for the model. We have also found that RH dependence of the signal is nearly zero at 40 C! This means that there is an optimum T for the measurement that is within reach of our temperature control for the improving accuracy.

Model C (Completely Self Contained T and RH Compensation):

Model B can be adapted for the situation in which the data show low dependence on RH. This leads to Model C, where the planes in FIG. 26 can be reduced to straight lines in the V$_{max}$-T plane, as shown in FIG. 28. Substituting w=0 in Equation 9 gives the following relationship:

$$h = \frac{A \cdot T + C \cdot V - d_0}{d_1} \quad (10)$$

For this situation, T and V$_{max}$ are the only measurable quantities which are required for a determination of the hydrogen concentration.

Table 4 shows the measured and calculated values of the hydrogen concentration using equation 10 and the data set collect in our experiments.

TABLE 4

Comparison of actual and calculated hydrogen concentration using Model C

| T (K) | % RH | [H$_2$] actual = 0.0% | [H$_2$] actual = 0.5% | [H$_2$] actual = 1.0% | [H$_2$] actual = 1.25% | [H$_2$] actual = 2.0% | [H$_2$] actual = 2.5% |
|---|---|---|---|---|---|---|---|
|  |  |  |  | [H$_2$] calculated |  |  |  |
| 294.702 | 2.647 | 0.046 | 0.63 | 1.149 | 1.402 | 2.136 | 2.528 |
| 302.407 | 14.298 | −0.125 | 0.408 | 0.919 | 1.203 | 1.973 | 2.399 |
| 284.374 | 70.895 | −0.143 | 0.484 | 1.017 | 1.269 | 1.999 | 2.42 |
| 295.102 | 34.593 | −0.048 | 0.569 | 1.095 | 1.337 | 2.068 | 2.547 |
| 301.89 | 22.586 | 0.022 | 0.574 | 1.096 | 1.349 | 2.107 | 2.538 |

The agreement of the calculated hydrogen concentration with the actual, indicates a relatively weak effect of RH on the sensor performance in the ranges considered. The compensation will be more accurate with the collection of additional data points in the calibration curve as herein, only a few points taken one time have been used. However, the printiciple and model have been clearly demonstrated mathematically and experimentally.

Selective Measurement of H$_2$ in the Presence of He

In addition to temperature and moisture, the application for H$_2$ detection includes potentially high levels of background helium. Differentiation of He from H$_2$ with a TCD has traditionally required separation via GC or MS. We evaluated the possibility of using the exemplary TCD in pulsed mode to discriminate between hydrogen and helium.

FIG. 29 illustrates the basic concept. By varying the current applied to the sensor, and thus the resulting T, the relative response to H$_2$ and He varies. At 2.5%, there is no detectable response to He below 1 mA, while we see response to hydrogen above 0.7 mA.

In practice, selectivity of H2 over He can be implemented by pulsing or scanning the sensor current over a range of, say, 0.5-1.4 mA. The relative response of the two gases at the different currents provides a signature that can be recognized. In principle, the slope of the temperature dependence of the TC can be obtained by operating at different currents [temperatures]. Since the slope for He and H2 are different, a smart sensor algorithm can be developed that differentiates H2 and He on the basis of the temperature dependence of the TC signal. Mixtures of H2 and He will have temperature coefficients in between the pure gases and therefore the slope of the temperature dependence will identify the mixture and the magnitude of the voltage excursion will quantitate the H2 and He per the above relationships. This approach provides and adaptation of Model C and the above calibration protocol explained for the temperature compensated benchmark TCD. What we have explained here is a path to a selective measurement of H2 in He for the exemplary TCD.

The model now provides for the specific detection of H2 in He, using data collected with the exemplary nanoTCD sensor and the temperature dependence of the TC. The CRC handbook lists the TC of gases at different temperatures. The non-ideal behavior of the TC of gas mixtures supports our novel and unique approach that the temperature dependence of the TC will be unique for gases and mixtures and provide unique calibration constants for our models and practical algorithm development. In this case we studied H2 in air, He in air and mixtures thereof at a series of different measurement currents [temperatures]. From the data in the exemplary pulsed mode, we obtain the $V_{max}$ and $V_{min}$ for the element. Using this we are able to calculate a Vave or Tave for representing the temperature at which the TC measurement is made. If we plot the Vmax [or TC signal] vs the Tave, the slope of this curve, C2, is unique for any gas or gas mixture which has a different temperature dependence of the TC [which includes all the gases in question herein].

C. Pd/Ni Coated Nano-TCD

Pd films are known to provide excellent sensitivity and preferential response to $H_2$ over other gases. For further enhancement of sensitivity and selectivity, we deposited a coating of Pd across the electrode gap on Dies #4, 5, and 6 The Pd sensor provides an additional approach to selective sensing of $H_2$ the presence of He.

Initially constructed Pd-coated structures did not have a functional polysilicon heater. Due to process issues, there is poor contact between the Pt and polysilicon however, several of the devices did have functional Pd films, and tests were run between 80-110 C using an oven to maintain the structure temperature. FIG. 30 depicts an example of a Pd coated Die 6. The polysilicon sensing element is visible as a green line and is 100 μm long, with a 50×1 μm center span. Although the Pd film (light brown rectangles) is off-center due to slight mask misalignment, it does coat the bridge between the Pt electrodes. Room temperature resistance of the Pd film varies from 500-700 ohm.

FIG. 31 illustrates the response of the Pd nano$H_2$ sensor to 0-2% $H_2$ at 80 and 100 deg C. Response is nearly the same at the two temperatures, but at 80 C the $H_2$ signal seems to flatten out more at 2%, so further testing of the sensor was done at 100 deg C.

The selectivity of the Pd-decorated nanostructure is illustrated in FIG. 32 with relative responses for hydrogen, He, and $CH_4$ (sensor T=100 C). He is not measurable even at 100%, and $CH_4$ is not detectable even at 5% in air or other diluent gas.

Conclusions:

These results clearly demonstrate the ability to fabricate a selective Pd-based $H_2$ sensor on our exemplary TCD platform and provide clear feasibility of discrimination of H2 and He for this nanostructure sensor element. In the present device, the very thin Pd film (500 A) exhibits largely surface effects rather than bulk effects, and has a high inherent resistance at the steps (Pt electrode edge), which are at ambient T rather than the sensing element T of 100 C.

D. HMOS Sensor for $CH_4$ [Demonstration of High Temperature Gas Sensor Feasibility]

In addition to hydrogen, NASA and other parties are interested in the selective detection of oxygen leaks and hydrocarbons—like CH4. Zirconium oxide and YSZ sensors are broadly used for $O_2$ detection and NASA has already developed high power designs of these chemistries for chemical sensing. Tin oxide has been shown to be responsive to $CH_4$ at temperatures of 300-400 C, which is within the temperature range of the materials used herein.

Structures 4, 5, and 6 all have Pt electrodes with a 50 μm gap. Rather than coating with Pd, one section of the wafer was coated with $SnO_2$. Sensors of the Die 4, 5, or 6 geometry were screened for functional polysilicon heaters, and intact $SnO_2$ coatings.

The optical micrographs in FIG. 33 show examples of Die 4, 5, and 6, with the $SnO_2$ coating. [Thin films of $SnO_2$ are transparent, but the edge of the film is visible as brown haze, due to refraction as light passes through the coating.

Determination of TCR for Heater Temperature Calculations:

One out of the 4 bridges on Dies 4 and 5 has a Pt RTD across the sensing element, to allow measurement of element temperature as a function of applied voltage or power. To calibrate the heater, the sensor was powered with a regulated voltage supply, and the heater voltage increased in increments while current, voltage, Pt and $SnO_2$ resistance were recorded. From the Pt resistance, temperature was calculated, using the standard TCR of 0.0039/deg C. Power was calculated from the applied current and voltage. Results are shown in FIG. 34.

The responsiveness of the $SnO_2$ coating was tested with mixtures of $CH_4$ in air, diluted from 5% $CH_4$ in nitrogen. The plots in FIG. 35 show a repeatable response to 4 and 5% $CH_4$. The sensor is noisy because of the step coverage of the electrodes. The repeatability of the structure is indicated both by the return to the same resistance in air (80 Mohm), as well as the repeatability of the bridge temperature and resistance as a function of applied power over repeated cycles.

Conclusion:

These results show that it is possible to construct a functional nano-TCD device with chemically selective HMOS coating that is compatible with the nano-TCD platform.

The TCD is based on a precision resistance measurement. The sensing element must be exceedingly stable and low noise, and the circuit must also be stable and precise/accurate. All wires and connections must be minimized and together with the electronic elements, stabilized. It is foreseeable that expect significant improvements in both detection limits and overall performance in field environments when the electronics and sensor package are minimized in both size and power. The step coverage issues for the sensing element electrodes will also be address by changing the die design contact [eliminating the step] from element to bond pad.

To prove this feasibility, we designed and built a $2^{nd}$ revision of the electronics for the Benchmark Posifa TCD sensor. The Rev2 board is small enough to fit inside a flame arrestor, to minimize extraneous resistances and capacitances as well as flow effects (see FIG. 36). Several tests were performed with the Benchmark sensor using this board, and it functions very well, being free from transients inside the test chamber. A typical series of cooling curves are shown in FIG. 37, the four overlain curves illustrate the excellent repeatability of the signal.

Pd and SnO$_2$ Coatings:

It is foreseeable that a plasma cleaning step can be added to improve adhesion and minimize contact resistance between electrodes and functionalization layers. In addition, thorough modeling of all layers, including coefficients of expansion, to minimize deformation and cracking can be performed to further optimize the present invention. Additionally, it is foreseeable to increase the thickness of the sensing layers to improve robustness and bulk properties. There have been numerous studies that illustrate the ppb level sensing capability of HMOS films and since we now have feasibility of our exemplary nanoTCD with coating, optimization should similarly enable selectivity and ppb-level detection.

The present exemplary embodiments can be useful in many applications:

Potential NASA Applications: In addition to cryogenic fuel gas leak sensors, these ultra-low power sensors will have applications wherever safety and loss prevention/cost minimization concerns are important.

Potential Non-NASA Commercial Applications:
Leak detection—hydrogen fueling stations, H$_2$ powered vehicles, H$_2$ production facilities-purge completion, etc.
Fuel Cells—process gas composition monitoring & process control, leak detection.

Particular embodiments of the monitoring device may further incorporate local and remote information readouts and/or alarms controlled by the various sensors and/or the central communication hub. The particular method or variety of alarm is not vital to the present invention, and examples include, but are not limited to, audible, visual and tactile alarms. Particular embodiments of the monitoring device may also incorporate global positioning system (GPS) technology and/or other positioning systems. Positioning system technology provides the central communication hub with first responder position history and tracking information for additional situational understanding. Positioning system technology may also be utilized to inform the central communication hub if any first responder has stopped moving for a particular period of time. While first responders (e.g., firefighters) are obvious users, there will be many other applications for a versatile and ultra low power gas detector with modern communication capability (e.g., wireless and internet based). Many apps will be able to be written around the enabling technology described herein, a major feature is the realization of ultra low power thereby achieving practicality in combining sensors and communication devices heretofore impossible and not realized.

The foregoing description of the various embodiments and principles of the invention has been presented for the purpose of illustration and description. It is not intended to be exhaustive or to limit the invention to the precise forms disclosed. Many alternative, modifications, and variations will be apparent to those skilled in the art. It can be envisioned by one skilled in the art both how to make alternative devices and layers for different functionality and also how to make this structure out of different materials like plastics with different processing tools and capabilities. For example, some principles of the invention may be used in different sensor platform patterns other than bridges. Moreover, although multiple inventive concepts have been presented, such aspects need not utilized in combination, and various combinations of the inventive aspects are possible in light of the various embodiments provided above. We can further provide examples of specific sensors like TCD [thermal conductivity detectors] or ozone or CO or H2S or even antibody detection with the platform described herein. There have been books dedicated to physical, chemical, and biological sensors wherein the functionalization layers are described and these can be interfaced to the MEMS platform described here to provide sensing capability. Accordingly, the above description is intended to embrace all possible alternatives, modifications, combinations and variations that have been discussed or suggested herein, as well as all the others that fall within the principles, spirit and broad scope of the invention as defined by the claims.

We claim:

1. A monitoring device, comprising:
   a. at least one sensor or sensing system utilizing microelectromechanical systems (MEMS) technology that consumes less than 500 µW of power;
   b. a processor;
   c. non-transitory computer readable medium tangibly embodying a set of executable instructions; and
   d. a power source;
   wherein the set of executable instructions is configured to cause the processor to:
      cause the power source to raise the power it consumes or operating temperature over a plurality of predetermined operating conditions over a prescribed time;
      receive corresponding electrical changes in a sensing element of the sensor over each of the plurality of predetermined operating conditions over time; and
      calculate target gas analyte composition for the received corresponding electrical changes.

2. The monitoring device of claim 1, wherein the electrical changes comprise resistance changes or voltage changes or combinations thereof.

3. The monitoring device of claim 1, wherein the calculation of target gas analyte composition is performed without any relative humidity (RH) dependence or temperature (T) dependence.

4. The monitoring device of claim 1, wherein the calculation of target gas analyte composition is performed using temperature (T) and relative humidity (RH) compensation using an embedded RH sensor in the sensor.

5. The monitoring device of claim 1, wherein the calculation of target gas analyte composition is performed using temperature (T) without the use of a relative humidity (RH) sensor.

6. The monitoring device of claim 2, wherein the act of causing the power source to raise its operating temperature comprises operating the power source in a pulsed mode.

7. The monitoring device of claim 5, wherein the target gas analyte is helium.

8. The monitoring device of claim 3, wherein the executable instructions are further configured to calibrate the sensor for temperature (T) correction and relative humidity (RH) correction; and wherein the executable instructions are further configured to cause the processor to:
   a. raise the operating temperature of the sensor from 10 degree C. to 30 degree C. in an environment free of RH by applying current to the sensor;
   b. calculate $R_{max}$ and $R_{min}$ at a plurality of the operating temperatures, wherein $R_{max}$ is the resistance of the sensor 0.4 ms after turning off current to the sensor and wherein $R_{min}$ is the resistance of the sensor 20 ms after turning off current to the sensor;
   c. calculating dR, wherein $dR=R_{max}-R_{min}$;
   d. calculating $R_{avg}$, wherein $R_{avg}=(R_{max}+R_{min})/2$;
   e. calculating $\lambda$, wherein $\lambda=R_{avg}/dR$;
   f. calculate C1 and B1, wherein C1 is the slope and B1 is the intercept of the regression of $R_{avg}/dR$ versus $R_{avg}$; and wherein $R_{avg}/dR=C1*R_{avg}+B1$.

9. The monitoring device of claim 8, wherein the executable instructions are further configured to cause the processor to:
a. calculate unknown percentage of hydrogen (%$H_2$) at any of the operating temperature of the sensor, wherein $$\%H_2=([R_{avg}/dR]_{unk}-[RaVg/dR]_{0\%H2}/(100*C''Ravg*Ravg+B'')),$$

wherein C" is the slope and B" is the intercept of regression of C' versus $R_{avg}$ and wherein C' is the slope of the regression of C1 versus % $H_2$.

10. The monitoring device of claim 9, wherein the executable instructions are further configured to cause the processor to:
a. obtain the resistance change of the sensor at a plurality of known concentrations of $H_2$;
b. obtain the resistance change of the sensor at a plurality of known concentrations of $H_2O$;
c. calculate a compensation factor (CF) for relative humidity;
d. calculate a compensated % $H_2$, wherein $$\%H_2=([R_{avg}/dR]_{unk}-[R_{avg}/dR]_{0\%H2})/(100*[C''_{avg}*R_{avg}+B''])-CF.$$

11. The monitoring device of claim 4, wherein the calculation comprises best-fit of the received resistance data to planar surfaces in 3 dimensions.

12. The monitoring device of claim 4, wherein the calculation comprises best-fit of the received voltage data to planar surfaces in 3 dimensions.

13. The monitoring device of claim 11, wherein causing the power source to raise its operating temperature comprises operating the power source in a pulsed mode.

14. The monitoring device of claim 13, wherein the target gas analyte is helium.

15. The monitoring device of claim 14, wherein the executable instructions are further configured to calibrate the sensor for temperature (T) correction and relative humidity (RH) correction; and wherein the executable instructions are further configured to cause the processor to:
a. raise the operating temperature of the sensor from 10 degree C. to 30 degree C. in an environment free of RH by applying current to the sensor;
  a. calculate $R_{max}$ and $R_{min}$ at a plurality of the operating temperatures, wherein $R_{max}$ is the resistance of the sensor 0.4 ms after turning off current to the sensor and wherein $R_{min}$ is the resistance of the sensor 20 ms after turning off current to the sensor;
  b. calculating dR, wherein $dR=R_{max}-R_{min}$;
  c. calculating $R_{avg}$, wherein $R_{avg}=(R_{max}+R_{min})/2$;
  d. calculating λ, wherein $\lambda=R_{avg}/dR$;
  e. calculate C1 and B1, wherein C1 is the slope and B1 is the intercept of the regression of $R_{avg}/dR$ versus $R_{avg}$; and wherein $R_{avg}/dR=C1*R_{avg}+B1$.

16. The monitoring device of claim 15, wherein the executable instructions are further configured to cause the processor to:
a. calculate unknown percentage of hydrogen (% $H_2$) at any of the operating temperature of the sensor, wherein $$\%H_2=([R_{avg}/dR]_{unk}-[Ravg/dR]_{0\%H2}/(100*C''Ravg*Ravg+B'')),$$

wherein C" is the slope and B" is the intercept of regression of C' versus $R_{avg}$ and wherein C' is the slope of the regression of C1 versus % $H_2$.

17. The monitoring device of claim 16, wherein the executable instructions are further configured to cause the processor to:
a. obtain the resistance change of the sensor at a plurality of known concentrations of $H_2$;
b. obtain the resistance change of the sensor at a plurality of known concentrations of $H_2O$;
c. calculate a compensation factor (CF) for relative humidity;
d. calculate a compensated % $H_2$, wherein $$\%H_2=([R_{avg}/dR]_{unk}-[R_{avg}/dR]_{0\%H2})/(100*[C''_{Ravg}*R_{avg}+B''])-CF.$$

18. The monitoring device of claim 1, wherein the at least one gas sensor senses a gas selected from the group consisting of hydrogen, helium, air, methane, carbon monoxide, hydrogen sulfide, chlorine, ozone, diesel particulates, gasoline fumes, ethanol, oxygen, carbon dioxide, and combinations thereof.

19. The monitoring device of claim 1, wherein the at least one sensor or sensing system utilizing MEMS technology comprises at least one surrounding environmental condition sensor.

20. The monitoring device of claim 18, wherein the at least one surrounding environmental condition sensor senses a surrounding environmental condition selected from the group consisting of temperature, pressure, radiation, moisture, and combinations thereof.

* * * * *

UNITED STATES PATENT AND TRADEMARK OFFICE
CERTIFICATE OF CORRECTION

PATENT NO. : 8,884,382 B2  Page 1 of 1
APPLICATION NO. : 13/868583
DATED : November 11, 2014
INVENTOR(S) : Joseph R. Stetter and Amol G. Shirke It is certified that error appears in the above-identified patent and that said Letters Patent is hereby corrected as shown below:

In the Claims

Col. 34, Line 62, "calculating dR" should read --calculate dR--;

Col. 34, Line 63, "calculating $R_{avg}$" should read --calculate $R_{avg}$--;

Col. 34, Line 64, "calculating λ" should read --calculate λ--;

Col. 35, Lines 6 and 7, "%$H_2$=([$R_{avg}$/dR]$_{unk}$-[RaVg/dR]$_{0\%H2}$/(100*C"Ravg*Ravg+B"])," should read --%$H_2$=([$R_{avg}$/dR]$_{unk}$-[$R_{avg}$/dR]$_{0\%H2}$)/(100*C"$R_{avg}$*$R_{avg}$+B"]),--;

Col. 35, Line 43, "a. calculate $R_{max}$" should read --b. calculate $R_{max}$--;

Col. 36, Line 1, "b. calculating dR" should read --c. calculate dR--;

Col. 36, Line 2, "c. calculating $R_{avg}$" should read --d. calculate $R_{avg}$--;

Col. 36, Line 3, "d. calculating λ" should read --e. calculate λ--;

Col. 36, Line 4, "e. calculate C1 and B1" should read --f. calculate C1 and B1--; and Col. 36, Lines 13 and 14, "%$H_2$=([$R_{avg}$/dR]$_{unk}$-[Ravg/dR]$_{0\%H2}$/(100*C"Ravg*Ravg+B"])," should read --%$H_2$=([$R_{avg}$/dR]$_{unk}$-[$R_{avg}$/dR]$_{0\%H2}$)/(100*C"$R_{avg}$*$R_{avg}$+B"]),--.

Signed and Sealed this
Twenty-third Day of June, 2015

Michelle K. Lee
*Director of the United States Patent and Trademark Office*